US010993433B2

(12) United States Patent
Pendergraft et al.

(10) Patent No.: US 10,993,433 B2
(45) Date of Patent: May 4, 2021

(54) METHOD OF PRODUCING IN VITRO TESTICULAR CONSTRUCTS AND USES THEREOF

(71) Applicant: Wake Forest University Health Sciences, Winston-Salem, NC (US)

(72) Inventors: Samuel Pendergraft, Winston-Salem, NC (US); Hooman Sadri-Ardekani, Lewisville, NC (US); Anthony Atala, Winston-Salem, NC (US); Colin Bishop, Clemmons, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 549 days.

(21) Appl. No.: 15/294,154

(22) Filed: Oct. 14, 2016

(65) Prior Publication Data
US 2017/0107483 A1 Apr. 20, 2017

Related U.S. Application Data

(60) Provisional application No. 62/242,046, filed on Oct. 15, 2015, provisional application No. 62/275,031, filed on Jan. 5, 2016.

(51) Int. Cl.
*C12N 5/22* (2006.01)
*A01N 1/02* (2006.01)
*C12N 5/071* (2010.01)

(52) U.S. Cl.
CPC .......... *A01N 1/021* (2013.01); *A01N 1/0221* (2013.01); *C12N 5/0697* (2013.01); *C12N 2506/246* (2013.01); *C12N 2510/04* (2013.01); *C12N 2533/90* (2013.01); *G01N 2500/10* (2013.01); *G01N 2510/00* (2013.01); *G01N 2520/00* (2013.01)

(58) Field of Classification Search
None
See application file for complete search history.

(56) References Cited

U.S. PATENT DOCUMENTS

| 5,376,542 A | 12/1994 | Schlegal |
| 5,811,281 A | 9/1998 | Quaroni et al. |

(Continued)

FOREIGN PATENT DOCUMENTS

WO WO-9502041 A1 * 1/1995 ............. C07K 14/80

OTHER PUBLICATIONS

Yu ("Essential Role of Extracellular Matrix (ECM) Overlay in Establishing the Functional Integrity of Primary Neonatal Rate Sertoli Cell/Gonocyte Co-cultures . . . ", Toxicological Sciences, 84, 378-393 (2005)) (Year: 2005).*

(Continued)

*Primary Examiner* — Robert J Yamasaki
*Assistant Examiner* — Charles Zoltan Constantine
(74) *Attorney, Agent, or Firm* — Myers Bigel, P.A

(57) ABSTRACT

A cell composition composed of spermatogonial stem cells, Sertoli cells, Leydig cells and optionally peritubular cells, is provided, as is a culture composition, artificial testicular construct, hydrogel composition, and device containing the same. A method for using the device as a physiologically relevant in vitro model of human testicular function to screen compounds for pharmacological or toxicological activity is also provided.

23 Claims, 15 Drawing Sheets

(56) References Cited

U.S. PATENT DOCUMENTS

| 6,387,133 | B1* | 5/2002 | Perouse | A61F 2/02 623/23.64 |
|---|---|---|---|---|
| 6,620,203 | B2 | 9/2003 | Atala | |
| 9,149,562 | B2 | 10/2015 | Shortkroff et al. | |
| 9,157,907 | B2 | 10/2015 | Grillari et al. | |

OTHER PUBLICATIONS

Hughes ("Matrigel: A complex protein mixture required for optimal growth of cell culture", Proteomics, 10, 1886-1890, 2010, and supplemental info) (Year: 2010).*
Tabuchi by ("Reconstruction of testicular function using immortalized cell lines with specific functions", Yakugaku Kenkyu no Shinpo, vol. 23, 2007, p. 25-29). (Year: 2007).*
Hoffman-2 ("Immortalization of Germ Cells and Somatic Testicular Cells Using the SV40 Large T Antigen", Experimental Cell Research, 201, 417-435, 1992). (Year: 1992).*
De Rooij DG. Proliferation and differentiation of spermatogonial stem cells. Reproduction, 2001. 121(3): p. 347-54.
Hofmann MC et al. Immortalized germ cells undergo meiosis in vitro. Proc Natl Acad Sci U S A, 1994. 91(12): p. 5533-7.
Wu N and Murono EP. A Sertoli cell-secreted paracrine factor(s) stimulates proliferation and inhibits steroidogenesis of rat Leydig cells. Molecular and Cellular Endocrinology, 1994. 106: p. 99-109.
Benton L et al. Differentiation of Adult Leydig Cells. J. Steroid Biochem. Molec. Biol., 1995. 53: p. 61-68.
Sato T et al. In vitro production of fertile sperm from murine spermatogonial stem cell lines. Nat Commun, 2011. 2: p. 472.
Huh D et al. From 3D cell culture to organs-on-chips. Trends in cell biology, 2011. 21(12): p. 745-54.
Sasai Y. Next-generation regenerative medicine: organogenesis from stem cells in 3D culture. Cell Stem Cell, 2013. 12(5): p. 520-30.
Easley 4th, CA et al. Direct differentiation of human pluripotent stem cells into haploid spermatogenic cells. Cell Rep. 2(3):440-6 (Sep. 2012).
Feng L et al. Generation and in vitro differentiation of a spermatogonial cell line. Science 297:392-5 (Jul. 19, 2002).
Aponte PM et al. Spermatogonial stem cells: characteristics and experimental possibilities. APMIS 113:727-42 (Nov.-Dec. 2005).
He Y et al. Developments in techniques for the isolation, enrichment, main culture conditions and identification of spermatogonial stem cells. Cytotechnology 67:921-30 (Epub Mar. 7, 2015).
Brinster RL and Zimmermann JW. Spermatogenesis following male germ-cell transplantation. Proc. Natl. Acad. Sci. U.S.A. 91:11298-302 (1994).
Brinster RL and Avarbock MR. Germline transmission of donor haplotype following spermatogonial transplantation, Proc. Natl. Acad. Sci. U.S.A. 91:11303-7 (1994).
Saldutti LP et al. In vitro testicular toxicity models: opportunities for advancement via biomedical engineering techniques. ALTEX 30(3); 353-377 (2013).
Sun J et al. Research on the isolation of mouse Leydig cells using differential digestion with a low concentration of collagenase. Journal of Reproduction and Development. 57(3): 433-436 (2011).
Chui K et al. characterization and functionality of proliferative human Sertoli cells. Cell Transplantation. 20: 619-635 (2011).
Sadri-Ardekani H et al. Propagation of human spermatogonial stem cells in vitro. JAMA. 302(19): 2127-2134 (Nov. 18, 2009).
3D Biomatrix(TM) Three-Dimensional Cell Culture product description white paper. 3D cell culture 101: an introdution to 3D cell culture tools and techniques. 3D Biomatrix, Ann Arbor, MI; 11 pp (2012).
Pendergraft SS et al. Three-dimensional testicular organoid: a novel tool for the study of human spermatogenesis and gonadotoxicity in vitro. Biology of Reproduction. 00(0): 1-13 (Feb. 2017).
Pendergraft S et al. Multicellular human testicular organoid: a novel in vitro germ cell and testicular toxicity model. Oral Abstracts. Andrology, 2015, Supplement, 45.
Sato T et al. In vitro production of functional sperm in cultured neonatal mouse testes. Nature, 2011. 471: 504-8.
Sadri-Ardekani H et al. In vitro propagation of human prepubertal spermatogonial stem cells. JAMA : the journal of the American Medical Association, 2011. 305(23): p. 2416-8.

* cited by examiner

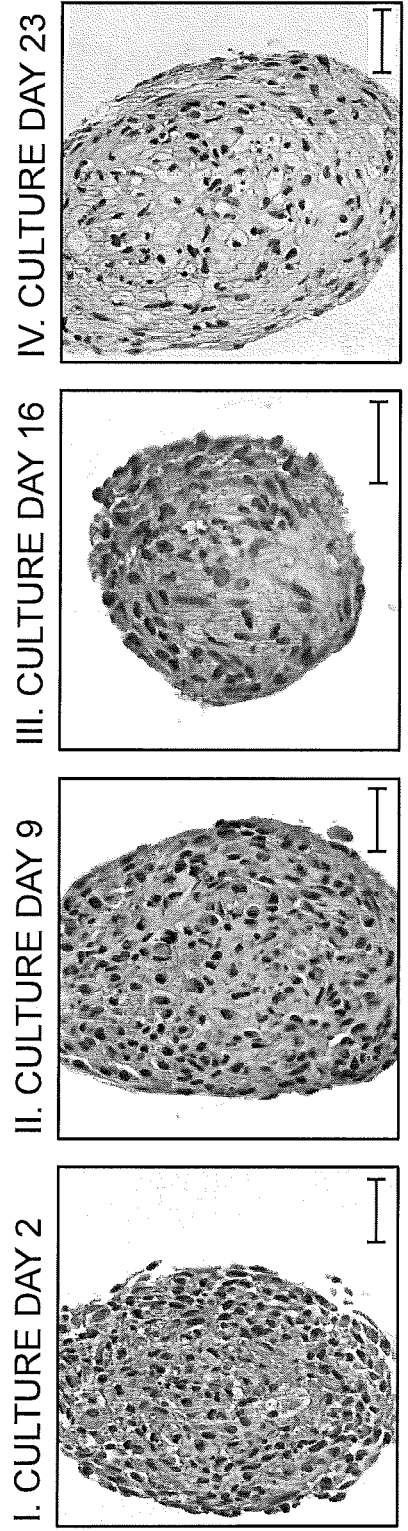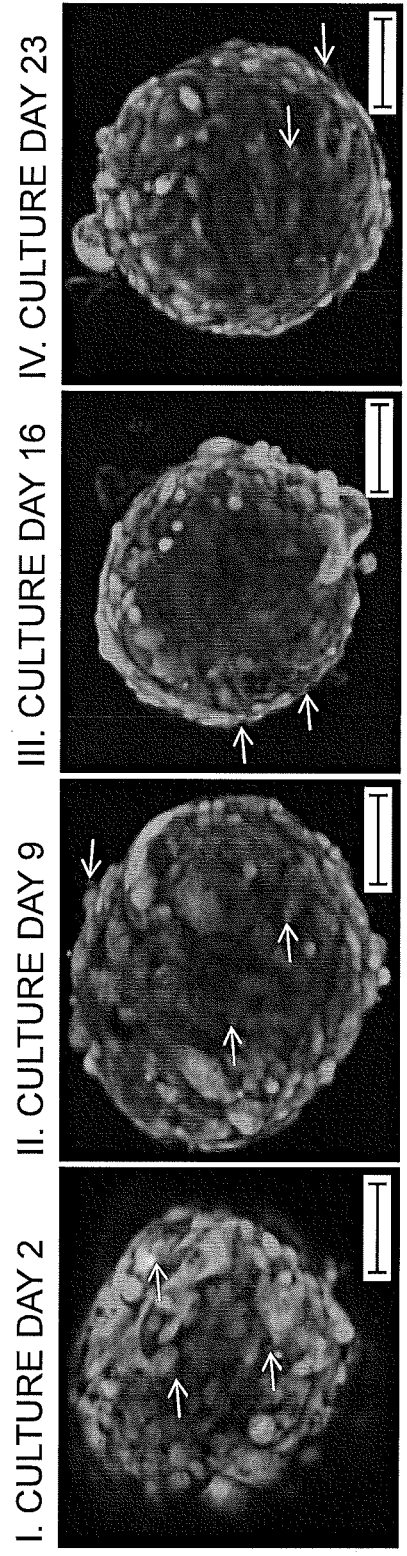
FIG. 5A
FIG. 5B

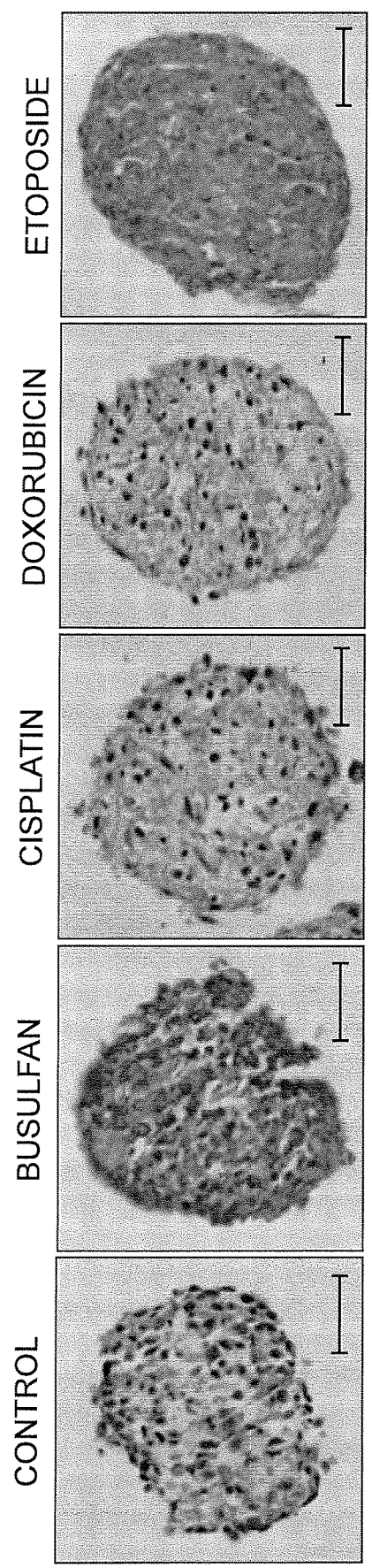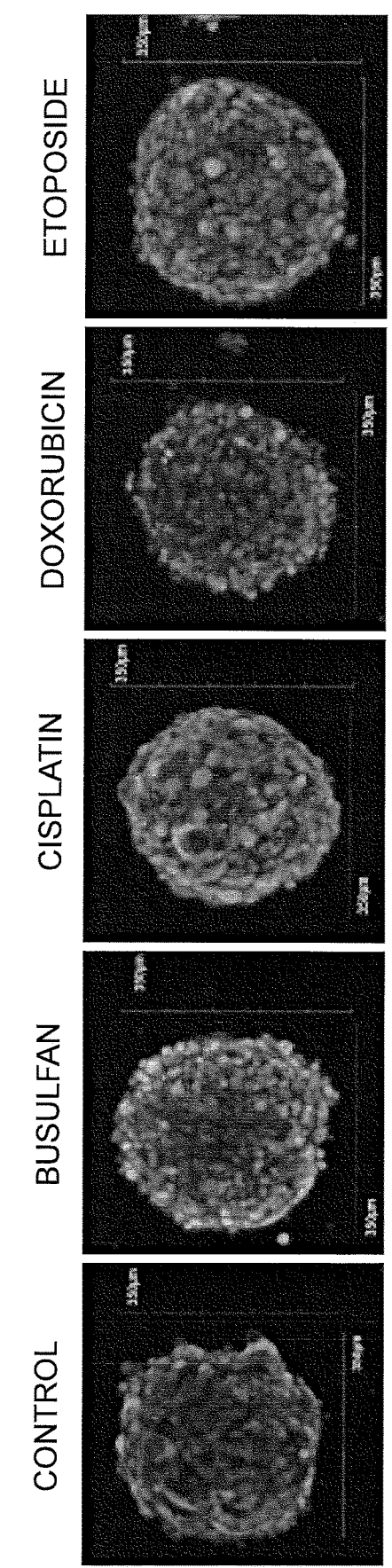
FIG. 7A
FIG. 7B

METHOD OF PRODUCING IN VITRO TESTICULAR CONSTRUCTS AND USES THEREOF

RELATED APPLICATIONS

This application claims the benefit of priority from U.S. Provisional Patent Application Ser. Nos. 62/242,046, filed Oct. 15, 2015, and 62/275,031, filed Jan. 5, 2016, the contents of which are incorporated herein by reference in their entireties.

GOVERNMENT SUPPORT

This invention was made with Government support under Grant No. W81XWH-13-2-0052 awarded by the Armed Forces Institute for Regenerative Medicine. The US Government has certain rights to this invention.

BACKGROUND OF THE INVENTION

The mammalian testis maintains an elaborate communication network between several cell types and subpopulations that cooperatively drive differentiation of male germ cells to haploid gametes, and the production of androgens via the process of steroidogenesis. This dual functionality reflects activities of two distinct testicular regions, the seminiferous tubules and interstitial tissue of the testis. Primitive spermatogonia confined to the basement membrane of the seminiferous epithelium develop in close contact with Sertoli cells. As spermatogonia progress from the basement membrane into the intermediate and adluminal compartments, they differentiate into spermatocytes and spermatids, eventually giving rise to mature sperm. Steroidogenesis is the biological process of steroid hormone synthesis from cholesterol precursors. Leydig cells are located in the testicular interstitium and secrete testosterone initiating the masculinization of the fetal gonad and maintaining post-pubertal spermatogenesis/spermatogenesis. The overall efficiency and success of spermatogenesis relies on the presence of the Sertoli cell-spermatogonial stem cell niche. This relationship between the developing germ cells and the surrounding testicular environment allows for the correct spatial arrangement of cells and enables them to receive and interpret the various signals and factors necessary for spermatogonial stem cell self-renewal and germ cell differentiation.

The isolation, characterization, and culture of testicular cells from rodents have been studied (de Rooij, D. G., *Proliferation and differentiation of spermatogonial stem cells*. Reproduction 121:347-354 (March 2001)). Culture systems composed of two-dimensional (2D) Sertoli-germ cell co-cultures incorporating extracellular matrix components have also been described (Hofmann, M. C., et al., Immortalized germ cells undergo meiosis in vitro. Proc. Natl. Acad. Sci. USA 91:5533-5537 (1994); Wu, N. & Murono, E. *A Sertoli cell-secreted paracrine factor(s) stimulates proliferation and inhibits steroidogenesis of rat Leydig cells*. Molecular and Cellular Endocrinology 106:99-109 (1994); Benton, L., et al., *Differentiation of Adult Leydig Cells*. J. Steroid Biochem. Molec. Biol. 53:61-68 (1995)). However, in these systems, the enzymatic digestion and mechanical disruption of native tissue required to isolate, characterize, and expand the various cell types often resulted in a loss of functionality and cell-type-specific gene expression. It also produced cells with markedly divergent phenotypes when compared to the defining in vivo characteristics of the tissue from which these cells are isolated (Huh, D., et al., *From 3D cell culture to organ-on-chips*. Trends in Cell Biology 21745-754 (2011); Sasai, Y., *Next-generation regenerative medicine: organogenesis from stem cells in 3D culture*. Cell Stem Cell 12:520-530 (2013)). Complete spermatogenesis in vitro has been reported in mice using decapsulated mouse testis in a soft-agar organ-culture method (Sato, T., et al., *In vitro production of fertile sperm from murine spermatogonial stem cell lines*. Nat. Commun. 2:472 (2011); Sato, T., et al., *In vitro production of functional sperm in cultured neonatal mouse testes*. Nature 471:504-507 (2011)). However, existing in vitro models are predominately inadequate for maintaining the highly complex signaling interactions of the mammalian testis. Currently, no human in vitro system exists that is able to support the paired functionality of both spermatogenesis and steroidogenesis within the same model system. There is recognizable need for such an in vitro system particularly for use in high-throughput and first-tier drug screening applications, as the number of potential human reproductive toxicants exceed current investigative capacities. See generally Saldutti, L., et al., *In Vitro Testicular Toxicity Models: Opportunities for Advancement via Biomedical Engineering Techniques*. ALTEX 30(3):353-377 (2013).

SUMMARY OF THE INVENTION

Described herein is a cell composition or culture composition, and artificial testicular construct containing the same, wherein said composition and construct include cells comprising, consisting essentially of, or consisting of, in combination:
  (a) spermatogonial stem cells,
  (b) Sertoli cells, preferably immortalized Sertoli cells, and
  (c) Leydig cells, preferably immortalized Leydig cells.

In some embodiments, said spermatogonial stem cells are included in an amount by number of cells of from 70 to 90 percent; said immortalized Sertoli cells are included in an amount by number of cells of from 5 to 20 percent; and said immortalized Leydig cells are included in an amount by number of cells from 5 to 20 percent.

In some embodiments, the ratio of spermatogonial stem cells to immortalized Sertoli cells to immortalized Leydig cells is 8:1:1.

In some embodiments, peritubular cells are also included (e.g., in an amount of from 0.01 or 0.05 to 3, 5 or 10% by number).

In some embodiments, the cells are mammalian cells, preferably human cells.

In some embodiments, the artificial testicular construct is produced via a scaffold-free platform.

In some embodiments, the artificial testicular construct has a diameter of 100 to 300 microns, or more preferably 200 to 250 microns.

In some embodiments, the total number of all cells in the artificial testicular construct is from 100 to 10,000, or more preferably from 1,000 to 2,000.

In further embodiments, the artificial testicular construct is characterized by:
  (i) the production or expression of testosterone by said construct;
  (ii) the expression of spermatogonial cell markers UCHL1, ITGA6, cKIT, DAZL, or a combination thereof;
  (iii) the expression of Leydig and Sertoli cell markers HSD3B1, CYP11a1, FSHr, CYP19a1, cKIT, or a combination thereof;

(iv) the expression of meiotic and post-meiotic markers SYCP3, PRM1, ACROSIN, or a combination thereof; or (v) a combination of (i)-(iv).

In some embodiments is provided a composition comprising a hydrogel, e.g., a crosslinked hydrogel, with a plurality of artificial testicular constructs in said hydrogel.

A device comprising a substrate having at least one chamber formed therein; and at least one artificial testicular construct (e.g., in a hydrogel) deposited in said chamber is also provided.

In some embodiments, said chamber has an inlet opening and outlet opening formed therein.

In some embodiments, the device is packaged in a container with a transient protective support medium in said chamber in gelled form, and optionally together with a cooling element in said container.

Methods of making and using the foregoing, for screening a compound for pharmacological or toxicological activity, are also disclosed herein.

BRIEF DESCRIPTION OF THE DRAWINGS

FIG. 1A. Reverse transcriptase polymerase chain reaction for spermatogonial cells markers: PLZF (promyelocytic leukemia zinc finger protein, ZTBT16), UCHL1 (ubiquitin carboxy-terminal hydrolase L1, or PGP 9.5), and THY1 (or cluster of differentiation 90, CD90). FIG. 1B. Sertoli cells markers: GATA4, CLU (clusterin), and SOX9. FIG. 1C. Leydig cells markers: STAR (steroidogenic acute regulatory protein), TSPO (translocator protein), and CYP11A1 (cholesterol side-chain cleavage enzyme) on whole testis (control) and isolated cells from the same patient. POLR2A (DNA-directed RNA polymerase II subunit RPB 1) was utilized as a reference marker in all cases. The second lane of each sample shows the negative reverse transcriptase (−RT) control. P5, passage 5.

FIG. 4A. Morphological characterization of multicellular human testicular organoids. Paraffin sections of testicular organoids stained by hematoxylin and eosin at low and high magnification are shown. FIG. 4B. Viability and proliferative capacity of multicellular human testicular organoids. Left: Live/Dead Confocal 3D Z-Stack projection of representative organoid after 2 days in culture. Right: Ki-67 Immunofluorescent staining of representative organoid paraffin section at day 2 of culture. FIG. 4C. Representative Confocal microscopy 3D Z-Stack projection of 3D testicular organoid using Vybrant™ Cell-Labeling Solutions. Incorporated testicular cell subtypes were individually labeled; (a) Spermatogonial stem cells (SSC), (b) Sertoli Cells, and (c) Leydig cells. FIG. 4D. Ultrastructural analysis of multicellular human testicular organoids using SEM to show exterior morphology. Left: representative testicular organoid showing entire 3D structure. Right: Representative high magnification image revealed complex cellular interactions and presence of lamellipodia. Scale bars represent 100 μm.

FIGS. 5A-5C. Testicular organoid morphological characterization and viability assessment. Morphological characterization of testicular organoids during extended culture (2, 9, 16 and 23 days). FIG. 5A. Paraffin sections of 3D cultures stained with hematoxylin and eosin for internal morphologic characterization revealed production of ECM within the organoids over time in culture without any sign of necrosis (Scale bar 100 μm). FIG. 5B. Organoids were stained using a Life Technologies Live/Dead Cell Imaging Kit (arrows=dead cells) and imaged using an Olympus FV10i confocal microscope. Scale bars represent 100 μm. FIG. 5C. Evaluation of ATP production using CellTiter-Glo® Luminescent Cell Viability Assays revealed consistent ATP production for the entire culture period (n=6). Data presented as mean±SD.

FIGS. 7A-7E. Morphological and viability assessment of human testicular 2D culture and 3D organoids following drug treatment. Representative hematoxylin and eosin (FIG. 7A) and confocal Live/Dead 3D Z-stack projection images (FIG. 7B) of 3D human testicular organoids (Scale bar, 100 μm) following drug exposure to busulfan, cisplatin, doxorubicin, and etoposide for 48 hours as compared untreated control. FIG. 7C. Drug effect on human testicular organoids. Undifferentiated and differentiated 3D cultures were exposed to drugs for 48 hours prior to determination of ATP content via CellTiter-Glo® Luminescent Cell Viability assays and subsequent generation of dose response curves (n=3). Data in graphs presented as mean±SD. FIG. 7D. Activation of caspase 3/7 in untreated and treated 3D testicular organoids following acute drug exposure. Luminescence produced by caspase 3/7 activity was measured following 48-hour incubation and cell viability (% control) was compared to non-treated controls incubated for the same exposure time (n=3). Data presented as mean±SD. Significance: *p<0.05; **p<0.01. FIG. 7E. TUNEL staining of testicular organoids following acute drug exposure. Scale bar=100 μm.

FIG. 8A. Representative phase contrast (top panel) and confocal Live/Dead (bottom panel) images of human testicular organoids cryopreserved by standard 8% DMSO, 20% FBS in MEM freezing media. Fresh organoid 2 days in culture (I, positive control) was compared to freeze/thawed organoids immediately after thawing (II), and following an additional 7 (III) and 14 days (IV) recovery in culture. These images were compared to cold-methanol treated organoids as a negative control (V). Cryopreserved organoids showed greater than 90% viability following thawing and subsequent to recovery in culture. (Scale bar 100 μm) FIG. 8B. Representative phase contrast (top panel) and confocal Live/Dead (bottom panel) images of human testicular organoids cryopreserved by vitrification method. Fresh organoid 2 days in culture (I, positive control) was compared to vitrified freeze/thawed organoids immediately after thawing (II), and following an additional 7 days (III) and 14 days (IV) recovery in culture. These images were compared to a cold-methanol treated organoid as a negative control (V). Vitrified organoids showed greater than 90% viability following thawing and subsequent culture (Scale bar, 100 μm).

FIG. 9A. Bright field microscopy. FIG. 9B. Live/Dead fluorescent staining (arrows=dead cells). FIG. 9C. Haematoxylin and Eosin staining. Scale bar 100 μm.

Figures 1A, 1B:
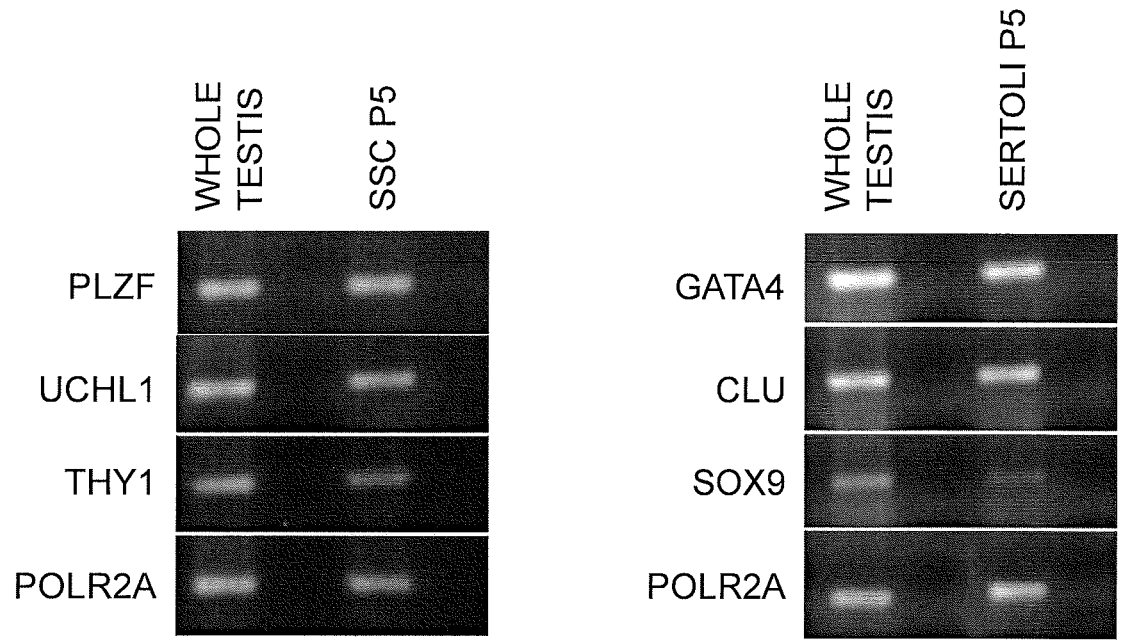
FIGS. 1A-1C. Characterization of spermatogonial stem cell (SSC), Sertoli, and Leydig cell markers in 2D cultures of human testicular cell subtypes.
Figure 1C:
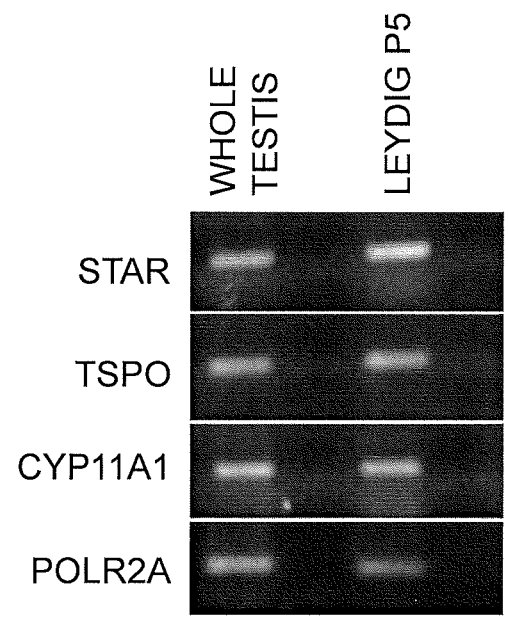

The present invention is explained in greater detail in the drawings herein and the specification set forth below. The disclosures of all United States patent references cited herein are to be incorporated by reference herein in their entirety.

DETAILED DESCRIPTION OF ILLUSTRATIVE EMBODIMENTS

It has now been found that upon combining SSC, Sertoli cells, Leydig cells and optionally peritubular cells, a 3D human testis organoid culture system is formed, which provides the requisite signaling interactions during spermatogenesis, thereby creating a more physiologically relevant in vitro model of human testicular function and for first-tier drug screening. Accordingly, this invention provides cell compositions, culture compositions, artificial testicular constructs and devices containing SSC, Sertoli cells, Leydig cells, and optionally peritubular cells, and methods of using the same in assessing pharmacological and/or toxicological activities of compounds.

The present invention is now described more fully with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey particular features and embodiments of the invention to those skilled in the art.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof.

As used herein, the term "and/or" includes any and all possible combinations or one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

"Cells," as used herein are, in general, mammalian cells, such as dog, cat, cow, goat, horse, sheep, mouse, rabbit, rat, etc. cells. In some preferred embodiments, the cells are human cells. Suitable cells are known and are commercially available, and/or may be produced in accordance with known techniques.

"Mammalian," as used herein refers to both human subjects (and cells sources) and non-human subjects (and cell sources or types), such as dog, cat, mouse, monkey, etc. (e.g., for veterinary purposes).

"Spermatogonial stem cells" or "SSC" denote undifferentiated male germ cells that have the potential to self-renew and differentiate into committed progenitors that maintain spermatogenesis throughout adult life. Spermatogonial stem cells can be isolated from the testis, as demonstrated herein, e.g., cryopreserved testicular tissue, or alternatively created from induced pluripotent stem cells or from embryonic stem cells. For example, culturing mammalian induced pluripotent stem cells and embryonic stem cells in standardized SSC culture conditions has been shown to provide undifferentiated spermatogonia. See, Easley, C. A. 4$^{th}$, et al., *Direct differentiation of human pluripotent stem cells into haploid spermatogenic cells*. Cell Rep. 2(3):440-6 (September 2012). Spermatogonial cell lines are known, and can be produced in accordance with any of a variety of known techniques. See, e.g., Feng, L., et al., *Generation and in vitro differentiation of a spermatogonial cell line*. Science 297: 392-5 (19 Jul. 2002); Aponte, P., et al., *Spermatogonial stem cells: characteristics and experimental possibilities*. APMIS 113:727-42 (November-December 2005); He, Y., et al., *Developments in techniques for the isolation, enrichment, main culture conditions and identification of spermatogonial stem cells. Cytotechnology* 67:921-30 (Epub 7 Mar. 2015). SSCs can be identified by a functional assay using a transplantation technique in which donor testis cells are injected into the seminiferous tubules of infertile recipient males (Brinster, R. L. & Zimmermann, J. W., *Spermatogenesis following male germ-cell transplantation*. Proc. Natl. Acad. Sci. U.S.A. 91:11298-302 (1994); Brinster, R. L. & Avarbock, M. R., *Germline transmission of donor haplotype following spermatogonial transplantation*. Proc. Natl. Acad. Sci. U.S.A. 91:11303-7 (1994)). Alternatively, or in addition to, SSC can be identified by the expression of one or more markers including, but not limited to germline-specific cell markers promyelocytic leukaemia zinc finger (PLZF), ubiquitin C-terminal hydrolase L1 (UCHL1), THY1 cell surface antigen, DEAD-Box Helicase 4 (DDX4, aka VASA), MAGE family member A4 (MAGEA4), and Ret proto-oncogene (RET).

"Sertoli cells," as used herein, refer to cells of the mammalian testis that are responsible for providing immune privilege. Sertoli cells are considered to be "nurse" or "chaperone" cells because they immunoprotect and assist in the development of germ cells into spermatozoa. The Sertoli cell maintains the "blood-testis" barrier (BTB) by forming occluding junctions that separate the tubules that comprise the seminiferous epithelium into two compartments. For a review on Sertoli cells, see, e.g., *Sertoli Cell Biology*, Skinner & Griswold (eds.), Elsevier Academic Press (2005). Sertoli cells can be isolated from the testis as described herein or using other established methods and provided as primary Sertoli cells, Sertoli cell lines or immortalized Sertoli cells. Sertoli cells can be identified functionally, e.g., by the production of inhibin, androgen-binding-protein (ABP), or antimüllerian hormone (AMH). Alternatively, or in addition to, Sertoli cells can be identified by the expression of one or more markers including, but not limited to, GATA binding protein 4 (GATA-4), clusterin (CLU), SRY-Box 9 (Sox9), follicle stimulating hormone receptor (FSHr), vimentin, Telomerase-associated protein 1 (TEP1), and Desert hedgehog (DHH).

"Leydig cells," as used herein, refer to the cells in the mammalian testis that contain two key steroidogenic enzyme pathways, namely, cytochrome P450 side chain cleavage (P450scc) and 3β-HSD. Leydig cells carry out the conversion of cholesterol, the substrate for all steroid hormones, to pregnenolone; and the conversion of pregnenolone to progesterone. Leydig cells can be isolated from the testis as described herein and be provided as primary Leydig cells, Leydig cell lines or immortalized Leydig cells. Leydig cells can be identified by the expression of one or more markers including, but not limited to, Cytochrome P450 Family 11 Subfamily A Member 1 (CYP11a1), 3β-Hydroxysteroid dehydrogenase (HSD3B1), Cytochrome P450 Family 19 Subfamily A Member 1 (CYP19a1), Steroidogenic Acute Regulatory Protein (STAR), translocator protein (TSPO), 7-dehydrocholesterol reductase (7-DHCR), and calreinin.

"Peritubular cells" or "peritubular myoid cells" refer to myofibroblast-like cells that surround the seminiferous tubules and are responsible for tubular contractility and sperm transport. Peritubular cells can be isolated from the testis as described herein and provided as primary peritubular cells, peritubular cell lines or immortalized peritubular cells. Peritubular cells can be identified by the expression of one or more markers including, but not limited to, CD34, inhibin beta-A, caldesmon 1 (CALD1) and tropomyosin 1 (TMP1).

The term "immortalization" is used herein to refer to cells that would normally not proliferate indefinitely but, due to genetic engineering, have evaded normal cellular senescence and can be grown for prolonged periods in vitro. A variety of methods exist for immortalizing mammalian cells. See, e.g., U.S. Pat. Nos. 9,157,907; 9,149,562; 5,811,281; and 5,376,542. One approach is to use viral genes, such as the simian virus 40 (SV40) T antigen, to induce immortalization (Jha, K. K., et al., *SV40-Meidated immortalization*. Exp. Cell Res. 245:1-7 (November 1998); Kirchhoff, C., et al. *Immortalization by large T-antigen of adult epididymal duct epithelium*. Mol. Cell Endocrinol. 216:83-94 (March 2004)). Alternatively, cell immortalization can be achieved through the expression of Telomerase Reverse Transcriptase protein (TERT), or TERT in combination with p53 or RB siRNA (Lundberg, A. S., et al., *Genes involved in senescence and immoralization*. Curr. Opin. Cell Biol. 12:705-9 (December 2005); Fridman, A. L. & Tainsky, M. A., *Critical pathways in cellular senescence and immortalization revealed by gene expression profiling*. Oncogene 27:5975-87 (October 2008); Yang, G., et al., *Knockdown of p53 combined with expression of the catalytic subunit of telomerase is sufficient to immortalize primary human ovarian surface epithelial cells*. Carcinogenesis 28:174-82 (January 2007); Yang, G., et al., *Disruption of the retinoblastoma pathway by small interfering RNA and ectopic expression of the catalytic subunit of telomerase lead to immortalization of human ovarian surface epithelial cells*. Oncogene 26:1492-8 (March 2007)). Retroviral, lentiviral and adenoviral vectors for hTERT, p53, RB, siRNA and SV40 T antigen-mediated cell immortalization are known in the art and readily available from commercial sources. See, e.g., *Applied Biological Materials General Guidelines for Cell Immortalization* (2015).

A "media" or "culture media," as used herein, refers to an aqueous based solution that is provided for the growth, viability, or storage of cells used in carrying out the present invention. A media or culture media may be natural or artificial. A media or culture media may include a base media and may be supplemented with nutrients (e.g., salts, amino acids, vitamins, trace elements, antioxidants) to promote the desired cellular activity, such as cell viability, growth, proliferation, and/or differentiation of the cells cultured in the media. A "base media," as used herein, refers to a basal salt nutrient or an aqueous solution of salts and other elements that provide cells with water and certain bulk inorganic ions essential for normal cell metabolism and maintains intra-cellular and/or extra-cellular osmotic balance. In some embodiments, a base media may include at least one carbohydrate as an energy source and/or a buffering system to maintain the medium within the physiological pH range. Examples of commercially available base media may include, but are not limited to, phosphate buffered saline (PBS), Dulbecco's Modified Eagle's Medium (DMEM), Minimal Essential Medium (MEM), Basal Medium Eagle (BME), Roswell Park Memorial Institute Medium (RPMI) 1640, MCDB 131, Click's medium, McCoy's 5A Medium, Medium 199, William's Medium E, insect media such as Grace's medium, Ham's Nutrient mixture F-10 (Ham's F-10), Ham's F-12, α-Minimal Essential Medium (aMEM), Glasgow's Minimal Essential Medium (G-MEM) and Iscove's Modified Dulbecco's Medium. See, e.g., US Patent Application Publication No. US20150175956.

The phrase "extracellular matrix proteins" (or "ECM proteins"), as used herein, collectively refers to secreted proteins that provide structural and biochemical support to a cell. The main fibrous ECM proteins include collagens (e.g., Types I, II, III, IV and V), elastins, fibronectins and laminins. Whereas collagens provide tensile strength, regulate cell adhesion, support chemotaxis and migration, and direct tissue development, fibronectin is involved in the organization of the interstitial ECM and mediating cell attachment and function, elastin provides recoil to tissues that undergo repeated stretch, and laminin influences cell differentiation, migration, and adhesion. In some embodiments, the ECM proteins are tissue-specific extracellular matrix proteins such as those described herein (Example 5) or in Y. Zhang et al., US Patent Application Publication No. 2013/0288375, the disclosure of which is incorporated by reference herein in its entirety. See also Skardal, A., et al., *Tissue specific synthetic ECM hydrogels for 3-D in vitro maintenance of hepatocyte function*. Biomaterials 33(18):4565-75 (2012).

"Hanging drop" methods of culturing cells, and apparatuses useful for the same, are known, and may be carried out in accordance with known techniques. See, e.g., U.S. Pat. No. 7,112,241; US Patent Application Publication Nos. 2003/0235519 A1, 2013/0040855 A1, 2014/0179561, and 2013/0084634 A1; and PCT Application Publication No. WO 2012/117083 A3.

"Hydrogel," as used herein, may be any suitable hydrogel. In general, the hydrogel includes water and is further comprised of or derived from polyalkylene oxides, poloxamines, celluloses, hydroxyalkylated celluloses, polypeptides, polysaccharides, carbohydrates, proteins, copolymers thereof, or combinations thereof, and more particularly are comprised of or derived from poly(ethylene glycol), poly(ethylene oxide), poly(vinyl alcohol), poly(vinylpyrrolidone), poly(ethyloxazoline), poly(ethylene oxide)-co-polypropylene oxide) block copolymers, carboxymethyl cellulose, hydroxyethyl cellulose, methylhydroxypropyl cellulose, polysucrose, hyaluronic acid, dextran, heparan sulfate, chondroitin sulfate, heparin, alginate, gelatin, collagen, albumin, ovalbumin, copolymers thereof, and combinations thereof, all of which are preferably cross-linked to varying degrees in accordance with known techniques, or variations thereof that are apparent to those skilled in the art. See, e.g., U.S. Pat. Nos. 8,815,277; 8,808,730; 8,754,564; 8,691,279.

A "substrate" is intended to include any biocompatible substrate, and may be biodegradable or non-biodegradable.

"Bioprinting" of cells, typically in a "bioink" such as a hydrogel (including but not limited to cross-linkable hydrogels), means utilizing three-dimensional, precise deposition of cells (e.g., cell compositions, cell-containing gels, cell cultures, cell concentrations, multicellular aggregates, multicellular bodies, etc.) via methodology that is compatible with an automated or semi-automated, computer-aided, three-dimensional prototyping device (e.g., a bioprinter). Bioprinting can be carried out in accordance with any of a variety of known methods and apparatuses. See, e.g., US Patent Application Publication No. 2008/0194010.

Cell Composition.

As noted above, the present invention provides a cell composition useful for making artificial testicular constructs. The composition includes, in combination: (a) spermatogonial stem cells (SSCs), (b) Sertoli cells, and (c) Leydig cells. The cells may be provided as primary cells, cell lines, or immortalized cells. In certain embodiments, the spermatogonial stem cells are provided as primary cells or as a spermatogonial cell line. In some embodiments, the Sertoli cells and Leydig cells are independently provided as primary cells, cell lines, or immortalized cells. In some embodiments, the cell composition further includes peritubular cells, which may be provided as primary cells, cell lines, or immortalized cells. The cells of the cell composition are generally mammalian cells, and preferably human cells.

The cells may be included in the composition in any suitable amount. In particular, the cell composition may be composed of:

(a) spermatogonial stem cells (primary cells or as a cell line) included in an amount by number of cells of from 70 to 90 percent, or more preferably 80 percent SSC cells;

(b) Sertoli cells (primary cells, immortalized cells or as a cell line) included in an amount by number of cells of from 5 to 20 percent, or more preferably 10 percent Sertoli cells; and (c) Leydig cells (primary cells, immortalized cells or as a cell line) included in an amount by number of cells of from 5 to 20 percent, or more preferably 10 percent, wherein percentages are based upon the total number of cells in the cell composition.

In certain embodiments, the cell composition includes spermatogonial stem cells, immortalized Sertoli cells, and immortalized Leydig cells at a ratio of 8:1:1.

Culture Composition.

In accordance with this invention, cell compositions are combined with an aqueous culture medium to provide a culture composition for use in making artificial testicular constructs. Generally, the culture medium is formulated to support the proliferation of stem cells in culture. Such a medium can be obtained commercially, e.g., STEMPRO-34 (available from Invitrogen), Pluripotent Stem Cell SFM XF/FF (available from ATCC), or derived from a stem cell culture medium known in the art. In addition to a basal medium, the culture medium can include additional components or supplements to support the cellular proliferation and/or development of testicular organoids. Such supplements include, but are not limited to, fetal bovine serum, B27 supplement, glial cell-derived neurotrophic factor (GDNF), basic fibroblast growth factor (bFGF), epidermal growth factor (EGF), stem cell factor (SCF) retinoic acid, follicle-stimulating hormone (FSH), an antibiotic, an antifungal, and the like.

In certain embodiments of this invention, the culture medium is supplemented with at least one ECM protein. In some embodiments, an ECM protein of the invention is that present in a testis extracellular matrix extract. In some embodiments, the ECM protein is that present in a human testis extracellular matrix extract. In some embodiments, the ECM protein is laminin, collagen type I, collagen type IV, fibronectin, elastin, or a combination thereof. In certain embodiments, the ECM protein is collagen type I. The ECM protein(s) may be included in any suitable amount, such as from 10 nanograms per milliliter to 1 milligram per milliliter. In particular, the ECM protein(s) may be included in an amount of 0.1 to 10 micrograms per milliliter, most preferably 1 microgram per milliliter.

Artificial Testicular Construct.

An artificial testicular construct or 3D testis organoid of this invention exhibits one or more biochemical and/or physiological characteristics of a testis. Accordingly, the artificial testicular construct finds use as a model of both spermatogenesis and steroidogenesis and can facilitate the evaluation of potential gonadotoxic agents in vitro. The construct is prepared from a cell composition or culture composition containing SSCs, Sertoli cells, Leydig cells, and optionally peritubular cells, by any suitable technique. In particular embodiments, the construct is prepared using a 3D cell culture technique. Examples of suitable 3D cell culture techniques include scaffold-free platforms for spheroid growth, scaffolds, gels, bioreactors, and microchips. See, e.g., 3D Biomatrix™ Three-Dimensional Cell Culture. *3D Cell Culture 101: An Introduction to 3D Cell Culture Tools and Techniques* (White paper). In particular embodiments, the artificial testicular construct is prepared using a scaffold-free platform. Scaffold-free aggregation of cells can be achieved by rotating well vessels (Ingram, M., et al. *Three-dimensional growth patterns of various human tumor cell lines in simulated microgravity of a NASA bioreactor*. In Vitro Cell Dev. Biol. Anim. 336:459-66 (1997)); cultivation in dynamic cell suspension contained in spinner flasks (Castaneda, F. & Kinne, R. K., *Short exposure to millimolar concentrations of ethanol induces apoptotic cell death in multicellular HepG2 spheroids*. J. Cancer. Res. Clin. Oncol. 1266:305-10 (2000); Foty, R. A. & Steinberg, M. S. *The differential adhesion hypothesis: a direct evaluation*. Dev. Biol. 2781:255-63 (2005)); maintenance in cell culture patterned surfaces or inserts; hanging drop culture by gravity-enforced assembly (Kelm, J. M., et al. *Method for generation of homogeneous multicellular tumor spheroids applicable to a wide variety of cell types*. Biotechnol. Bioeng. 832:173-80 (2003)); liquid overlay method (Enmon, R. M., Jr., et al. *Dynamics of spheroid self-assembly in liquid-overlay culture of DU 145 human prostate cancer cells*. Biotechnol. Bioeng. 726:579-91 (2001); Metzger, W., et al., *The liquid overlay technique is the key to formation of co-culture spheroids consisting of primary osteoblasts, fibroblasts and endothelial cells.* Cytotherapy 138:1000-12 (2011)) or micro-fluidics (Okuyama, T., et al. *Preparation of arrays of cell spheroids and spheroid-monolayer cocultures within a microfluidic device*. J. Biosci. Bioeng. 1105:572-6 (2010)). In conventional scaffold-free platforms, biomaterials and ECM are not exogenously added, as the cells that grow in the scaffold-free platform typically generate and organize their own ECM (Chua, C. K. & Yeong, W. Y. *Bioprinting: Principles and Applications*. New Jersey: World Scientific, pg. 184 (2015). However, in accordance with certain embodiments of this invention, one or more ECM proteins are added to the cells of the scaffold-free platform. Scaffold-free platforms are known in the art and can be obtained from a number of commercial sources. Examples of such systems include, but not limited to, GravityPLUS™ Hanging Drop System (InSpero Inc., Brunswick, Me.) and Perfecta3D® Hanging Drop System (3D Biomatrix, Ann Arbor, Mich.).

The artificial testicular construct may have a diameter of 100 to 300 microns, or more preferably 200 to 250 microns. The total number of all cells in the construct may be from 100 to 10,000 cells or more preferably between 1,000 to 2,000 cells. Construct size and cell numbers can be determined as exemplified herein or using any other suitable technique known in the art.

In some embodiments, the construct may be characterized by:
  (i) the production or expression of testosterone by said construct;
  (ii) the expression of spermatogonial cell markers UCHL1, Integrin subunit alpha 6 (ITGA6), KIT proto-oncogene receptor tyrosine kinase (cKIT), and/or Deleted in Azoospermia Like (DAZL);
  (iii) the expression of Leydig and Sertoli cell markers HSD3B1, CYP11a1, FSHr, CYP19a1, cKIT, and/or CYP11a1; and/or
  (iv) the expression of meiotic and post-meiotic markers Synaptonemal Complex Protein 3 (SYCP3), protamine 1 (PRM1), and/or ACROSIN.

When the construct includes peritubular cells, the construct may also be characterized by the expression of CD34. Markers can be detected using any suitable immunological technique, e.g., flow cytometry for membrane-bound markers, immunohistochemistry for intracellular markers, and enzyme-linked immunoassay for markers secreted into the medium. The expression of protein markers can also be detected by western blot analyses or at the mRNA level by, e.g., reverse transcriptase-PCR using conventional marker-specific primers.

Methods of Making Artificial Testicular Constructs.

In some embodiments, artificial testicular constructs may be made by using spheroid culture methods (i.e., scaffold-free aggregate culture methods). The spheroid culture methods may be useful for co-culture, in which cells may organize themselves into distinct layers. Specifically, hanging drop culture methods may be used to make self-assembled cellular aggregate structures representing artificial testicular constructs. Hanging drop culture methods may include depositing droplets including the culture composition onto a culture substrate (e.g., a hanging drop plate) and then culturing the cells in the culture composition. In some embodiment, the hanging drop culture methods may optionally include turning the culture substrate over before culturing the cells. Hanging drop culture methods allow the cells to form an aggregate in the bottom of a droplet hanging from a surface of the substrate. Foty, Ramsey, *A Simple Hanging Drop Cell Culture Protocol for Generation of 3D Spheroids*, Journal of Visualized Experiments: JoVE, no. 51. doi: 10.3791/2720 (2011). Hanging drop culture methods may be able to produce uniform sizes of tissue based on the number of cells seeded in the drop. See, e.g., Mehta et al., *Opportunities and Challenges for Use of Tumor Spheroids as Models to Test Drug Delivery and Efficacy*, Journal of Controlled Release 164 (2): 192-204 (2012). Commercial hanging drop plates from InSphero (Schlieren, Switzerlan) and 3D Biomatrix (Ann Arbor, Mich., USA) may be used to generate artificial testicular constructs. However, any methods that facilitate close cell-cell contacts in the absence of interacting substrates may be used, such as gravity-enforced self-assembly methods (See, e.g., Kelm et al., Trends Biotechnol. 2004, 22:195-202) or methods using microfabricated molds (See, e.g., Yeon et al., PLos One 2013, 8(9), e73345).

Hydrogel Compositions.

Constructs or organoids described above can be used per se, or the constructs or organoids can be combined with a hydrogel, such as a cross-linkable hydrogel, e.g., to facilitate manipulation and handling of the constructs. Suitable hydrogels are known and include, but are not limited to, those described in Skardal, A., et al., *A hydrogel bioink toolkit for mimicking native tissue biochemical and mechanical properties in bioprinted tissue constructs*. Acta Biomater. 25:24-34 (2015). In some embodiments, a cross-linked hyaluronic acid hydrogel (optionally including additional polymers such as gelatin) is used.

Hydrogels fall into two main categories: naturally-derived hydrogels and synthetic hydrogels. Naturally-derived hydrogels and synthetic hydrogels may be mixed to form hybrid hydrogels. Naturally-derived hydrogels may include Matrigel®, which is made out of native extracellular matrix proteins collected from a cell line, as well as collagen and alginate. Naturally-derived hydrogels may use decellularized tissue extracts. Extracellular matrix may be collected from a specific tissue and may be combined with a hydrogel material to be used to support cells of that tissue type. See, e.g., Skardal et al., *Tissue Specific Synthetic ECM Hydrogels for 3-D in vitro Maintenance of Hepatocyte Function*, Biomaterials 33 (18): 4565-75 (2012). Chitosan hydrogel is an example of a naturally-derived hydrogel that is degradable and supportive for several different cell types. See, e.g., Moura et al., *In Situ Forming Chitosan Hydrogels Prepared via Ionic/Covalent Co-Cross-Linking*, Biomacromolecules 12 (9): 3275-84 (2011). Hyaluronic acid hydrogels may also be used. See, e.g., Skardal et al., *A hydrogel bioink toolkit for mimicking native tissue biochemical and mechanical properties in bioprinted tissue constructs*, Acta Biomater. 25: 24-34 (2015).

Synthetic hydrogels may be produced from a variety of materials (e.g., Poly-(ethylene glycol)) and using many techniques. In contrast to naturally-derived hydrogels, synthetic hydrogels may be produced uniformly and may be easily reproducible and characterized. Synthetic hydrogels may, however, lack some functional signals for cells, like the active sites found in natural extracellular matrix, limiting their potential to support cells. See, e.g., Mahoney et al.,

*Three-Dimensional Growth and Function of Neural Tissue in Degradable Polyethylene Glycol Hydrogels*, Biomaterials 27 (10): 2265-74 (2006). Hybrid hydrogels may offer a compromise and may allow for more control over the ability to reconstruct a specific microenvironment. By combining natural components, such as extracellular matrix molecules (e.g., extracellular matrix proteins), with defined synthetic hydrogels, a more easily reproducible and functional hydrogels can be produced. See, e.g., Salinas et al., *Chondrogenic Differentiation Potential of Human Mesenchymal Stem Cells Photoencapsulated within Poly(Ethylene Glycol)-Arginine-Glycine-Aspartic Acid-Serine Thiol-Methacrylate Mixed-Mode Networks*, Tissue Engineering 13 (5): 1025-34 (2007).

Devices.

In some embodiments, the artificial testicular construct exists in a chamber or well of a biocompatible device. Devices useful for in vitro compound screening with constructs or organoids of the invention typically are produced by (a) providing a substrate or device body (e.g., a microfluidic device) having at least one chamber formed therein (the chamber preferably having an inlet and outlet opening formed therein); and (b) depositing at least one construct as described above (per se, or as a composition thereof in combination with a hydrogel) in the chamber. The depositing step may be carried out by any suitable technique, such as bioprinting, pipetting, microinjection, microfluidic deposition, etc. In some embodiments, a construct is placed into a chamber. In some embodiments, a construct is bioprinted into a chamber. In further embodiments, the chamber is coated. In various further embodiments, the chamber is coated with one or more of: a biocompatible hydrogel, one or more proteins, one or more chemicals, one or more peptides, one or more antibodies, or one or more growth factors, including combinations thereof. In some embodiments, the construct exists on a porous, biocompatible membrane within a chamber of the device. The device may be provided in the form of a cartridge for "plug in" or insertion into a larger apparatus including pumps, culture media reservoir(s), detectors, and the like.

In some embodiments, the device includes an array of artificial testicular constructs. In some embodiments, an "array" is a scientific tool including an association of multiple elements spatially arranged to allow a plurality of tests to be performed on a sample, one or more tests to be performed on a plurality of samples, or both. In some embodiments, the arrays are adapted for, or compatible with, screening methods and devices, including those associated with medium- or high-throughput screening. In further embodiments, an array allows a plurality of tests to be performed simultaneously. In some embodiments, an array allows a plurality of constructs, e.g., of different genetic backgrounds, to be tested simultaneously. In some embodiments, the constructs of the array are spatially arranged in a pre-determined pattern. In various embodiments, patterns of arrangement include, by way of non-limiting examples, a two-dimensional grid, a three-dimensional grid, one or more lines, arcs, or circles, a series of rows or columns, and the like. In further embodiments, the pattern is chosen for compatibility with medium- or high-throughput biological assay or screening methods or apparatuses.

In some embodiments, the construct is affixed to the device. In accordance with such embodiments, securing of a construct to the device on one or more sides facilitates subjecting the construct to shear force. Such shear force can be caused by, e.g., fluid flow, recirculation, perfusion, or agitation of the liquid nutrients that contact the construct on one or more exposed surfaces.

The device is preferably biocompatible in that it is composed of any suitable material or combination of materials which do not pose a significant risk of injury or toxicity to the construct. Examples of suitable materials include, but are not limited to, polydimethylsiloxane (PDMS), polystyrene, polymethyl methacrylate (PMMA), polyacrylamide, polyethylene glycol (PEG) including functionalized PEG (e.g., PEG diacrylate, PEG diacrylamide, PEG dimethacrylate, etc., or any of the foregoing PEGs in multi-arm forms, etc.), natural polymers or proteins that can be cross-linked or cured (e.g., hyaluronic acid, gelatin, chondroitin sulfate, alginate, etc., including derivatives thereof that are functionalized with chemical groups to support cross linking), and combinations thereof. The device may be formed by any suitable process, including molding, casting, additive manufacturing (3D printing), lithography, etc., including combinations thereof. For example, microfabrication techniques such as those disclosed in U.S. Publication No. 2011/0015739, entitled "Systems and Methods for Forming Patterned Extracellular Matrix Materials," can be used to form the device or other components used to form the device. Using the techniques disclosed in US 2011/0015739, a stamp can be used to form chambers in a first polymer layer. After inserting the constructs, the chambers can be sealed by providing a second polymer layer thereover, although the second polymer layer may include openings or pores to allow communication between the constructs and the host environment. Alternatively, microfabrication techniques, such as those disclosed in U.S. Publication No. 2008/0286482, entitled "Forming or Patterning Composite Microstructures Using Microfluidics," and in U.S. Publication No. 2010/0278798, entitled "Methods and Systems for Forming Biocompatible Materials," can be used to form the device or other components used to form the device. Using the device disclosed herein, a genetically homogenous panel of artificial testicular constructs or genetically heterogeneous panel of artificial testicular constructs (alone or in combination with any other cell line or tissue) can be micropatterned into a millimeter-sized cassette. Such a device can facilitate the assessment of drug or treatment efficacy thereby reducing the cost and time of drug testing.

Storing and Shipping of Devices.

Once produced, devices as described above in cartridge form may be used immediately, or prepared for storage and/or transport. To store and transport the product, a transient protective support medium that is a flowable liquid at room temperature (e.g., 25° C.), but gels or solidifies at refrigerated temperatures (e.g., 4° C.) may be used. Such a support medium can include, e.g., gelatin mixed with water. Alternatively, to store and transport the product, a transient protective support medium that is a flowable liquid at cooled temperature (e.g., 4° C.), but gels or solidifies at warm temperatures such as room temperature (e.g., 20° C.) or body temperature (e.g., 37° C.) is used. Examples of materials used in such a support medium include, e.g., poly(N-isopropylacrylamide) and poly(ethylene glycol) block co-polymers.

The transient protective support medium is added into the device to substantially or completely fill the chamber(s), and preferably also any associated conduits. Any inlet and outlet ports can be capped with a suitable capping element (e.g., a plug) or capping material (e.g., wax). The device is then packaged together with a cooling element (e.g., ice, dry ice, a thermoelectric chiller, etc.) and all placed in a (preferably insulated) package. Upon receipt, the end user simply removes the device from the associated package and cooling element, allows the temperature to rise or fall (depending on the choice of transient protective support medium), uncaps any ports, and removes the transient protective support medium with a syringe (e.g., by flushing with growth media).

Methods of Use of Devices.

Devices described above can be used for in vitro screening (including medium- or high-throughput screening) of a compound (or compounds) for pharmacological and/or toxicological activity. Such screening can be carried out by: (a) providing a device as described above; (b) administering a compound to the construct (e.g., by adding to a growth media being flowed through the chamber containing the construct); and then (c) detecting a pharmacological and/or toxicological response to the compound from at least one cell of the construct. The response of the construct to the compound can be detected by any suitable technique, including microscopy, histology, immunoassay, etc., including combinations thereof, depending on the particular response, or set of responses, being detected. Such response or responses may be cell death (including senescence and apoptosis), cell growth (e.g., benign and metastatic cell growth), absorption, distribution, metabolism, or excretion (ADME) of the compound, or a physiological response (e.g., upregulation or downregulation of production of a compound by the at least on cell), or any other biological response relevant to pharmacological and/or toxicological activity.

In some embodiments, the assay is carried out in a larger apparatus including one or more detectors or imaging devices and a processor configured to determine, based on the images from the imaging device, characteristics of each construct that relate to the response of the construct to the compound thereon. For example, the processor can be configured to determine at least one of organoid diameter, change in organoid size, viable cell mass, percentage viability, and pathway activity. Using conventional image processing techniques, the processor can identify the organoid in the platform and determine a size thereof. The size can then be compared with a previously determined size of the organoid to determine if the organoid has grown, stayed the same, or reduced in size.

The present invention is explained in greater detail in the following non-limiting Examples.

Example 1

Human Testis Material

Human testis tissue was obtained from The National Disease Research Interchange (NDRI). Testicular tissue was used for human testis extracellular matrix (ECM) extraction or cut into small segments to be used for cryopreservation and immunohistochemical testing. For cryopreservation, tissue fragments (~2-5 mm) were frozen in 1× minimum essential medium containing 8% DMSO, 20% fetal bovine serum (FBS) slowly overnight using a Mr. Frosty container inside a −80° C. freezer. Cryotubes were moved to liquid nitrogen (−196° C.) for long-term storage. For all of cell isolations, cryopreserved tissue was used. Tissue pieces used for immunohistochemical staining were fixed in 4% paraformaldehyde and paraffin-embedded. Morphology of testes, stained by Hematoxylin and Eosin (H&E), showed normal spermatogenesis in all patient samples used in this study. All human materials in this study were used under regulation and approval of Institutional Review Board (IRB) of the Wake Forest School of Medicine.

Example 2

Testicular Cell Isolation, Culture and Cryopreservation of Spermatogonial Stem Cell (SSC) Lines Preparation and Culturing of SSC.

Spermatogonial cell lines were isolated and cultured as previously described using a modified SSC propagation media that included growth factors necessary for maintenance of spermatogonia in their undifferentiated state (Sadri-Ardekani, H., et al., *Propagation of human spermatogonial stem cells in vitro*. JAMA: The Journal of the American Medical Association, 302(19):2127-34 (2009); Sadri-Ardekani, H., et al., *In vitro propagation of human prepubertal spermatogonial stem cells*. JAMA: The Journal of the American Medical Association, 305(23):2416-8 (2011)) Briefly, previously cryopreserved testicular tissue segments of about 100 mg to 200 mg were thawed and enzymatically digested using a combination of collagenase, hyaloronidase, and trypsin. A two-step enzymatic digestion was performed and isolated testicular cells were cultured at 37° C., 5% $CO_2$ on uncoated dishes in supplemented 1×MEM (1×MEM with 10% FBS, 1× nonessential amino acids (Invitrogen, Carlsbad, Calif.), 15 mM HEPES (Invitrogen), 50 µg/mL gentamycin (Invitrogen), 4 mM L-glutamate (Invitrogen), 0.12% sodium bicarbonate, streptomycin (100 µg/mL)—penicillin (100 IU/mL) (Sigma, St. Louis, Mo.)) overnight and floating cells were differentially plated onto uncoated 6-well plates at a seeding density of 5000-20000 cells/cm$^2$ in supplemented StemPro®-34 (Invitrogen) medium (Stempro®-34 with recombinant human GDNF (40 ng/mL) (Sigma), recombinant human EGF (20 ng/mL), recombinant human Leukemia inhibitory factor (10 ng/mL), streptomycin (100 µg/mL)—penicillin (100 IU/mL) (Sigma)). Medium was refreshed every 96 hours and cells were passaged upon becoming 80% confluent (usually every 7-10 days) into new 6-well culture plates at a seeding density of 5000-20,000 cells/cm$^2$. Residual somatic cells from initial isolation were utilized as a feeder layer for proliferating germ cells. Excess cells were cryopreserved at −196° C. using a 1×MEM cryopreservation media containing 20% FBS, 8% DMSO.

RT-PCR Characterization.

In order to verify the presence of spermatogonia, total RNA from primary spermatogonial stem cell cultures and whole testis tissue from the same patient (positive control) was isolated using an RNeasy® Mini Kit (QIAGEN, Valencia, Calif.) with on-column DNase I digestion using the QIAGEN RNase-Free DNase Kit following manufacturer's recommendations. RNA was converted to cDNA using a high-capacity cDNA Reverse Transcription Kit (Life Technologies, Carlsbad, Calif.), with 500 ng RNA as input. For reverse transcriptase PCR (RT-PCR) analysis, Taqman® gene expression assays were used (Life Technologies). Reactions were performed using standard Taqman® Universal PCR Master Mix (96-well plate format) and an ABI 7500 FAST system (Life Technologies). For each Taqman® assay, 50 ng cDNA was used per well. Cycling conditions were as follows: 95° C. for 10 min, 95° C. for 15 seconds (40 cycles), and 60° C. for 1 minute. Analysis and relative gene expression changes were determined using GraphPad Prism® software. All runs were performed in duplicate.

Example 3

Testicular Cell Isolation, Culture, Immortalization and Cryopreservation of Primary Human Sertoli Cell Lines Preparation and Culturing of Sertoli Cell Lines. Human Sertoli cells were isolated from human tissue as previously described by Chui et al. (Chui, K., et al., *Characterization and functionality of proliferative human Sertoli cells*. Cell Transplant 20(5):619-35(2011)). Briefly, testicular samples were obtained within 24 hours of death. These tissues were washed first with ice-cold calcium/magnesium-free Hank's balanced salt solution (HBSS) containing 100 U/mL penicillin and 100 µg/mL streptomycin. The tunica albuginea was removed and separated brown tubule tissue was transferred to an Erlenmeyer flask in HBSS. These tissues were shaken at 275-325 rpm for 15 minutes to separate the interstitial cells from the tubules. The supernatant was removed following removal from shaker and 0.25% trypsin and 0.1% collagenase type IV (Sigma) were added with 300 rpm shaking for 20 minutes at 37° C. The dissociated cells were then strained through a coarse wire mesh (1 mm$^2$) with the flow through being stored on ice. Soybean trypsin inhibitor was added and the complete homogenate was passed through an 18-gauge needle and centrifuged at 800 g for 5 minutes. The cell pellet was then resuspended in DMEM/F-12 Ham's medium containing penicillin and streptomycin with a final concentration of 5% FBS. Cells were propagated in the same medium in a 5% $CO_2$ incubator at 37° C.

Nile Red Staining.

Nile Red staining for lipid droplets was carried out using a modified method described by Fowler et al. (Fowler, S., & Greenspan, P., *Application of Nile red, a fluorescent hydrophobic probe, for the detection of neutral lipid deposits in tissue sections: comparison with oil red O*. J. Histochem. Cytochem 33(8):833-6 (1985)). Sertoli cells were seeded in 8-chamber slides and cultured to 80% confluency. At this point, a 1 mM stock solution of Nile Red was prepared in anhydrous DMSO. From this solution, a 200-1000 nM working solution was prepared by dilution in Dulbecco's phosphate-buffered saline (PBS) with vortexing. Adherent Sertoli cells were washed with 1×PBS and Nile Red working solution was added directly to the cells and incubated at room temperature for 5-10 minutes. Fluorescence changes at Excitation/Emission=552/636 were observed using a fluorescence microscope.

RT-PCR.

To determine the presence of Sertoli cells, total RNA from isolated primary Sertoli cell cultures and whole testis tissue from the same patient (positive control) was isolated using an RNeasy® Mini Kit (QIAGEN), with on-column DNase I digestion using the QIAGEN RNase-Free DNase Kit following manufacturer's recommendations. RNA was converted to cDNA using a high-capacity cDNA Reverse Transcription Kit (Life Technologies), with 500 ng RNA as input. For reverse transcriptase PCR (RT-PCR) analysis, Taqman® gene expression assays were used for Sertoli cell-specific markers including Clusterin, Sox9, and Gata4 (Life Technologies). Reactions were performed using standard Taqman® Universal PCR Master Mix (96-well plate format) and an ABI 7500 FAST system (Life Technologies). For each Taqman® assay, 50 ng cDNA was used per well. Cycling conditions were as follows: 95° C. for 10 min, 95° C. for 15 seconds (40 cycles), and 60° C. for 1 minute. The gene POLR2A was used as an internal control. Analysis and relative gene expression changes were determined using GraphPad Prism® 6 software. All runs were performed in duplicate.

Immunohistochemistry/Immunofluorescence.

Immunohistochemical and immune-fluorescent staining to determine the presence of Sertoli cells was performed using isolated human Sertoli cells cultured on 4-well chamber slides (Nalgene Nunc International Corp., Rochester, N.Y.). Cultured cells were washed in 1×PBS and fixed in 4% paraformaldehyde for 30 minutes on ice. Cells were washed 3 times in 1×PBS and permeabilized using 0.2% Triton™ X-100 for 10 minutes prior to blocking for 30 minutes at room temperature in Dako® serum-free protein block. Excess protein block was removed and cells were incubated with primary anti-Vimentin (Dako M0725, 1:200), anti-SOX9 (1:300), or anti-Telomerase-associated protein 1 (sc-166620; Santa Cruz Biotechnology, Santa Cruz, Calif.; 1:100) antibodies overnight at 4° C. Negative controls were species-specific IgG diluted to the same concentration as the primary antibody. Fluorescent signal was visualized on cultured cells using a stepwise incubation with biotinylated goat anti-rabbit biotin (1 hour at room temperature, 1:300 dilution) and streptavidin-Alexa Fluor® 488 (1 hour at room temperature, 1:200 dilution), and counterstained using Vectorshield® mounting media with 4',6-diamidino-2-phenylindol (DAPI). Immunohistochemical signal was visualized on cultured cells using a Powervision™ diaminobenzidine (DAB) Chromagen solution (Leica Biosystems, Newcastle, UK). Slides were visualized on a Zeiss Axiovert 200M fluorescence/live cell-imaging microscope.

Lentiviral Immortalization.

Isolated primary human Sertoli cells at passage 2 were immortalized via lentiviral transduction using a bicistronic vector encoding hTERT and a puromycin-resistance cassette. Puromycin-selected cells were expanded and monitored for 10 passages to ensure that the immortalization protocol did not have a negative effect on growth, morphology, or gene expression Immortalized human Sertoli cells from passages 3-6 were used for all subsequent experiments.

Example 4

Testicular Cell Isolation, Culture, Immortalization and Cryopreservation of Primary Human Leydig Cell Lines Preparation and Culturing of Leydig Cell Lines. Leydig cells were isolated from human tissue using a modified protocol as previously described by Sun et al. (Sun, J., et al., *Research on the isolation of mouse Leydig cells using differential digestion with a low concentration of collagenase*. J. Reprod. Dev. 57(3):433-6 (2011)). This protocol was modified for use with human tissue. Briefly, testis material was rinsed with PBS and the tunica albuginea was removed. The resulting testis tubules were moved to a 50 mL conical tube and digested in a solution of 0.03% collagenase type IV for 15 minutes with 200 rpm shaking at 37° C. Following this step, the cells were pelleted and resuspended in another volume of 0.03% collagenase type IV for 15 minutes with 120 rpm shaking at 37° C. The supernatant containing interstitial cells and Leydig cells was moved to a separate tube and centrifuged at 1500 rpm for 5 minutes at 23° C. This cell pellet was resuspended in a low glucose DMEM with 10% FBS and 50 µg/mL Gentamycin and seeded in 6-well tissue culture plates incubated at 37° C. under 5% $CO_2$.

3Beta-Hydroxysteroid Dehydrogenase (3B-HSD) Staining.

Staining for 3B-HSD was accomplished using an established protocol. Briefly, Leydig cells were cultured for 24 hours on 4-well or 8-well chamber slides (Nalgene Nunc International Corp, Rochester, N.Y.) and washed three times in PBS. Solutions A (1 mg NBT, 0.6 mg DHEA, and 0.6 mL DMSO) and B (10 mg B-NAD and 9.5 mL PBS) were mixed and added directly to the cells and incubated at 37° C. for 2 hours. Positive staining was indicated by the presence of dark violet particles within the cell cytoplasm.

RT-PCR.

To determine the presence of Leydig cells, total RNA from isolated primary testicular cell cultures and whole testis tissue from the same patient (positive control) was isolated using an RNeasy® Mini Kit (QIAGEN, Valencia, Calif.), with on-column DNase I digestion using the QIAGEN RNase-Free DNase Kit following manufacturer's recommendations. RNA was converted to cDNA using a high-capacity cDNA Reverse Transcription Kit (Life Technologies), with 500 ng RNA as input. For reverse transcriptase PCR (RT-PCR) analysis, Taqman® gene expression assays were used for Leydig cell-specific markers STAR, TSPO, and CYP11A1 (Life Technologies). Reactions were performed using standard Taqman® Universal PCR Master Mix (96-well plate format) and an ABI 7500 FAST system (Life Technologies). For each Taqman® assay, 50 ng cDNA was used per well. Cycling conditions were as follows: 95° C. for 10 min, 95° C. for 15 seconds (40 cycles), and 60° C. for 1 minute. The gene POLR2A was used as an internal control. Analysis and relative gene expression changes were determined using GraphPad Prism® software. All runs were performed in duplicate.

Lentiviral Immortalization.

Isolated primary human Leydig cells at passage 2 were immortalized via lentiviral transduction using a bicistronic vector encoding hTERT and a puromycin resistance cassette. Puromycin-selected cells were expanded and monitored for 10 passages to ensure that the immortalization protocol did not have a negative effect on growth, morphology, or gene expression Immortalized human Leydig cells from passages 3-6 were used for all subsequent experiments.

Immunohistochemistry/Immunofluorescence.

Isolated human Leydig cells were cultured on 4-well chamber slides (Nalgene Nunc International Corp, Rochester, N.Y.). Cultured cells were washed in 1×PBS and fixed in 4% paraformaldehyde for 30 minutes on ice. Cells were washed 3 times in 1×PBS and permeabilized using 0.2% Triton® X-100 for 10 minutes prior to blocking for 30 minutes at room temperature in Dako® serum-free protein block. Excess protein block was removed and cells were incubated with primary anti-HSD3B1 (1:100), anti-INSL3 (1:100), or anti-Telomerase-associated protein 1 (sc-166620; Santa Cruz Biotechnology, Santa Cruz, Calif.; 1:100) antibodies overnight at 4° C. Negative controls were species-specific IgG diluted to the same concentration as the primary antibody. Fluorescent signal was visualized on cultured cells using a stepwise incubation with biotinylated goat anti-rabbit biotin (1 hour at room temperature, 1:300 dilution) and either streptavidin-Alexa Fluor® 488 or streptavidin-Alexa Fluor® 594 (1 hour at room temperature, 1:200 dilution), and counterstained using Vectorshield® mounting media with DAPI. Cells were visualized on a Zeiss Axiovert 200M fluorescence/live cell-imaging microscope.

Androgen Production.

Androgen production was measured using a testosterone high sensitivity enzyme-linked immunosorbent assay (ELISA) kit (ENZO Testosterone high sensitivity 96-well enzyme immunosorbent assay kit, Enzo life sciences, Farmingdale, N.Y.) according to the manufacturer's instructions. The minimum detectable limit was 3.9 pg/mL. Cell culture supernatant was concentrated 4× using an Eppendorf® Vacufuge® and all samples were assayed in duplicate. A standard curve was generated and used to determine testosterone concentrations. Testosterone levels were determined via optical density at 405 nm wavelength absorbance.

Example 5

Decellularization of Human Testis Tissues and ECM Extraction

Fresh testis tissues obtained from the NDRI were first pre-rinsed briefly in cold DPBS. The tunica albuginea was left intact for this procedure and the entire testis organ was cut into 2 cm by 2 cm slices and sectioned into roughly 2 mm slices. All of the slices were then moved to 500 mL containers in ultrapure water and shaken on a rotary shaker at 4° C. for 3 days at 200 rpm. During this time ultrapure water was changed three times per day. After 72 hours the water was replaced with 2% Triton® X-100 for approximately 4 days. This solution was changed twice daily and subsequently replaced with a solution of 2% Triton® X-100 containing 0.1% $NH_4OH$, with shaking at 200 rpm for 24 hours. This solution was then removed and the tissues were washed to remove remaining Triton® X-100 detergent. Decellularized ECMs were frozen at −80° C. and lyophilized for 48 hours. The lyophilized tissues were ground using a freezer mill, and 400 mg ECM was subsequently mixed with 40 mg Pepsin (Porcine gastric mucosa, 3400 units; Fisher Scientific, Fair Lawn, N.J.). To this mixture, 0.1N hydrochloric acid was added and incubated for 48 hours at room temperature. The suspension was neutralized to pH 7.2 using NaOH and filter-sterilized through a 0.2 μm filter and stored at −80° C. until further use.

Example 6

Methods for Forming, Culturing and Characterizing Human Testicular Organoids

Testicular Organoid Formation.

Isolated human SSC, immortalized Sertoli cells, and immortalized Leydig cells at passage 5-6 were propagated in normal 6-well tissue culture plates to 80-90% confluency and passaged using trypsin EDTA (0.25%). Counted cells were pelleted and resuspended in a testicular organoid formation medium composed of normal StemPro®-34 (Invitrogen) SSC proliferation medium supplemented with 30% FBS, 1 μg/mL solubilized human testis extracellular matrix extract and 50 μg/mL Gentamycin. All three cell suspensions were combined together at a ratio of 8:1:1 and seeded into Perfecta3D® 96-well hanging drop plates (3D Biomatrix, Ann Arbor, Mich.) or GravityPLUS™ 96-well hanging drop plates (InSphero, Schlieren, Switzerland) at a density of 10,000 cells/40 μl drop volume. Following 48-72 hours of hanging drop culture, all testicular cell subtypes had amalgamated into compact organoids and were transferred into 96-well format Corning® Costar® Ultra-low Attachment Multiwell U-bottom plates for long term culture (Sigma-Aldrich, St. Louis, Mo.). For long-term study, all testicular organoids were cultured inn normal StemPro®-34 SSC proliferation medium without human leukemia inhibitory factor (LIF) and supplemented with 1 μg/mL solubilized human testis extracellular matrix extract, 2 µM retinoic acid (Sigma-Aldrich), $2.5 \times 10^{-5}$ IU follicle-stimulating hormone (Sigma-Aldrich), 100 ng/mL recombinant human stem cell factor (SCF; PeproTech, Rocky Hill, N.J.), and 50 µg/mL Gentamycin. Culture medium was refreshed every 4 days. All testicular organoids were cultured at 34° C. and 5% $CO_2$.

Viability.

Organoid viability was determined using a combination of Molecular Probes Live/Dead® Cell Imaging (Invitrogen) and ATP content (CellTiter-Glo® Luminescent Cell Viability Assay; Promega, Madison, Wis.). For the Live/Dead assay, organoids were harvested, washed 3 times with 1×PBS, and were imaged using an Olympus FV10i Confocal microscope 15 minutes after adding calcein AM (green fluorescent dye retained by live cells) and ethidium homodimer (red fluorescent dye taken up by dying and dead cells). To evaluate organoid ATP production, 8 organoids were harvested per time point and transferred to single well so luminescence-compatible 96-well plates (Nalgene NUNC International Corp., Rochester, N.Y.) in 100 µl of culture media. To each well, 100 µl of CellTiter-Glo® reagent was added and mixed for 5 minutes on a rotary shaker. Signal was measured using a luminometer. Viability was monitored for the duration of the 23-day culture period (days 2, 9, 16, and 23).

Histology.

Human testis organoids were harvested for analysis at days 2, 9, 16, and 23 of culture. At each time point, organoids were pooled and fixed in 4% paraformaldehyde for 30 minutes at room temperature. Fixed organoids were embedded in HistoGel™, paraffin-embedded, and 5 µM sections were prepared. These sections were deparaffinized and H&E staining was performed according to standard protocols. Organoids were visualized on a Zeiss Axiovert 200M fluorescence/live cell-imaging microscope.

Proliferation.

To evaluate the proliferation activity of cells in testis organoids, immunohistochemistry using KI-67 was performed. Paraffin sections of organoids were deparaffinized and then antigen retrieval was performed for 15 minutes in 0.01 M sodium citrate, pH 6.0 at 98° C. To permeabilize the membranes of cells, a 10 minute incubation in 0.2% Triton® X-100 was performed. To block nonspecific binding, slides were incubated in Protein Block Serum-Free (Dako) 15 minutes prior to starting an overnight incubation of Ki-67 antibody (Abcam; rabbit anti-Ki-67 polyclonal) at 4° C. Ki-67 antibody was pre-diluted 1:50 in antibody diluent (Dako). This was followed by a 1 hour incubation of goat anti-rabbit biotinylated antibody (Vector Laboratories) pre-diluted to 1:200 in antibody diluent (Dako). Finally, slides were incubated for 1 hour in streptavidin-Alexa Fluor® 594 (Thermo-Fisher Scientific) and counterstained with Fluoroshield™ DAPI (Sigma-Aldrich). All wash steps were performed using PBS, pH 7. Unless otherwise noted, incubation was at room temperature. All slides were imaged using a Olympus Fluoview FV10i confocal microscope.

Evaluation of Internal Cellular Organization of Human Testicular Organoids.

To evaluate cell type-specific organization within organoids formed using all three isolated testis cell subtypes, a Vybrant™ Multicolor Cell-Labeling Kit (Thermo Fisher) was used to fluorescently mark each cell type prior to organoid formation and culture, following the manufacturer's instructions. Briefly, SSC, Sertoli, and Leydig cells were passaged separately and suspended at a density of $1 \times 10^6$ cells/mL in 1 mL DMEM F-12 serum-free culture medium containing 5 µL of either DiO, DiI, or DiD cell labeling solution. Cells were incubated for 15 minutes at 37° C. to produce uniform staining profiles. Cells were then washed three times and used directly to form testicular organoids as described herein. Resulting cell-labeled testicular organoids were subsequently evaluated for internal morphological changes and cell identification using a Leica TCS LSI Macroconfocal microscope.

Ultrastructural Analysis of 3D Organoids Using Scanning Electron Microscopy (SEM).

For ultrastructural analysis, organoids were harvested at set time points and pooled in groups of 40-50 organoids per condition. Medium was removed and organoids were washed twice in 15 ml 1×PBS via sedimentation. Organoids were then fixed with 2.5% glutaraldehyde in PBS for 2 hours at room temperature. Glutaraldehyde was removed and organoids were washed in 15 ml $diH_2O$ twice to remove fixative and transferred into 1.5 ml microfuge tubes for further processing. Testicular organoids fixed in 2.5% glutaraldehyde for SEM analysis were dehydrated in graded ethanol solutions diluted in DI water while maintaining a constant 1:20 sample to ethanol solution ratio. Briefly, organoids were treated in a 50% ethanol solution for 20 minutes, 70% ethanol for 20 minutes, 80% ethanol for 20 minutes, 90% ethanol for 20 minutes, 95% ethanol for 20 minutes, and finally 100% ethanol for 60 minutes (changed every 20 minutes). Samples were mounted, further dehydrated via critical point drying, and gold sputter-coated. Coated samples were then used immediately for SEM following normal microscopy protocols.

Reverse Transcriptase Quantitative PCR (RT-qPCR).

RNA from the appropriate tissue or cells was isolated using an RNeasy® Mini Kit (QIAGEN, CA). RNA was converted to cDNA using a high-capacity cDNA Reverse Transcription Kit (Life Technologies), with 500 ng RNA as input. ABI Taqman® gene expression assays were used for all qPCR gene expression assays (Life Technologies) according to the manufacturer's instructions. The POLR2A gene was used as an internal control. Reactions were performed using standard Taqman® Universal PCR Master Mix (96-well plate format) and an ABI 7500 FAST system (Life Technologies). For each Taqman® assay, 50 ng cDNA was used per well. Cycling conditions were as follows: 95° C. for 10 min, 95° C. for 15 seconds (40 cycles), and 60° C. for 1 minute. All runs were performed in duplicate. Expression of all genes was normalized to POLR2A gene; relative expression (e.g., comparing day 2 and 23 of organoid culture) was determined with the MCT method.

Immunofluorescence for Germ Cell Differentiation Markers.

Samples were deparaffinized, then permeabilized with 0.2% Triton® X-100 (Sigma) and put through microwave antigen retrieval (AR6 buffer; Perkin Elmer). Spheroid sections were blocked for 10 minutes with serum-free protein block (Dako), and then stained in antibody diluent (Dako) overnight at 4° C. with primary antibody (Rabbit Anti-human Acrosin, diluted 1:3000 or rabbit Anti-human PRM1, diluted 1:125 both from Sigma-Aldrich). Following several washes with Tris-buffered saline (TBST), sections were then incubated with goat anti-rabbit, HRP-labeled antibody (Perkin Elmer) for 1 hour at room temperature. Following three washes with TBST, sections were treated with Tyramide Signal Amplification (TSA) Plus Fluorescence working solution and selected fluorophore (Perkin Elmer) for 10 minutes at room temperature (Fluorescein for PRM1 and Cyanine 5.5 for Acrosin). Slides were then washed three times and stained with DAPI (Perkin Elmer) for 5 minutes. Slides were subsequently washed again with TBST. Prolong® gold mounting medium (Life Technologies) in combination with Gold Seal® coverslips (Electron Microscopy Sciences) were used for coverslip application. All slides were imaged with FV1200 Laser Scanning Confocal Microscope.

Testosterone Production.

Organoid androgen production was measured using a testosterone high sensitivity ELISA kit (ENZO Testosterone high sensitivity 96-well enzyme immunosorbent assay kit; Enzo Life Sciences, Farmingdale, N.Y.) according to the manufacturer's instructions. The minimum detectable limit was 3.9 pg/mL A total of 20 organoids per time point were used in this assessment, wherein half were stimulated with 2 nM hCG for 3 hours. Following incubation, cell culture supernatant was collected from stimulated and nonstimulated organoids and concentrated 4× using an Eppendorf® Vacufuge®. All samples were assayed in duplicate. A standard curve was generated and used to determine testosterone concentrations. Testosterone levels were determined via optical density at 405 nm wavelength absorbance.

Drug Toxicity Test.

For toxicity testing, cisplatin and etoposide were purchased from Santa Cruz Biotechnology (Dallas, Tex.) and stock solutions of 5 mM and 25 mM were made in 0.9% NaCl and DMSO, respectively. Doxorubicin was purchased from Sigma-Aldrich, (St. Louis, Mo.) and a stock solution was produced in diH$_2$O at a concentration of 10 mM. Busulfan (24 mM) was purchased from Otsuka Pharmaceutical (Tokyo, Japan) and was diluted into medium immediately prior to use. The undifferentiated (just after formation, 2 days in culture) and differentiated (23 days in culture) organoids, as well as 2D cultured cells (at the same cell ratios and density of 3D organoids), were treated for 48 hours in 6 different concentrations of each drug (0.01, 0.1, 1, 10, 100 and 1000 µM) in vitro. After 48 hours, CellTiter-Glo® Luminescent Cell Viability assays were performed (Promega) on all conditions. Briefly, culture plates were removed from the incubator and equilibrated to room temperature for 30 minutes. To each well of the 96-well culture plate, 100 µl of CellTiter-Glo® reagent was added at a 1:1 ratio and plates were moved to an orbital shaker for 5 minutes to induce cell lysis. Plates were incubated at room temperature for 10 minutes to stabilize luminescent signal and read on a Veritas™ luminometer. Integration times of 1 second were used for all samples. All conditions were performed in triplicate and medium only control wells were read and subsequently used for background subtraction. IC$_{50}$ values were determined using GraphPad Prism® 6 calculated via 4-parameter fit with a 95% confidence interval. All experimental conditions were repeated at least three times.

Statistical Analyses.

Statistical analysis of all quantitative results is presented as mean±standard deviation (SD). Statistical significance was determined using Student's t test, with p values <0.05 considered statistically significant. Statistics were determined using GraphPad Prism® 6 software.

Example 7

Methods for Cryopreservation and Thawing of Testicular Organoids

Standard Cryopreservation.

Following 48-72 hours of hanging drop culture and subsequent transfer to 96-well Corning® Costar® Ultra-low Attachment Multiwell U-bottom plates, organoids were harvested, pooled, and cryopreserved in 8% DMSO and 20% FBS in 1×MEM using a Mr. Frosty™ freezing container. Organoids were thawed after 7 days at −196° C. using a stepwise dilution of cryoprotectant medium into a normal organoid culture medium containing 30% FBS. Organoids were allowed to recover in this medium for 1 hour prior to transfer to 96-well Ultra-low Attachment Multiwell U-bottom plates and resuming of normal culture conditions.

Vitrification.

Following 48-72 hours of hanging drop culture and subsequent transfer to 96-well Corning® Costar® Ultra-low Attachment Multiwell U-bottom plates, organoids were harvested, pooled, and vitrified using a vitrification freeze kit for human embryos (Vit Kit®-Freeze; Irvine Scientific, Santa Ana, Calif.) according to manufacturer's recommendations. Organoids were thawed after 7 days at −196° C. using a vitrification thaw kit for human embryos (Vit Kit®-thaw; Irvine Scientific) following manufacturer's recommendations (Vit Kit®-thaw; Irvine Scientific). Organoids were then moved to 96-well Ultra-low Attachment Multiwell U-bottom plates and normal culture conditions were resumed.

Example 8

Formation and Characterization of Multicellular Human Testicular Organoids

Figure 2:
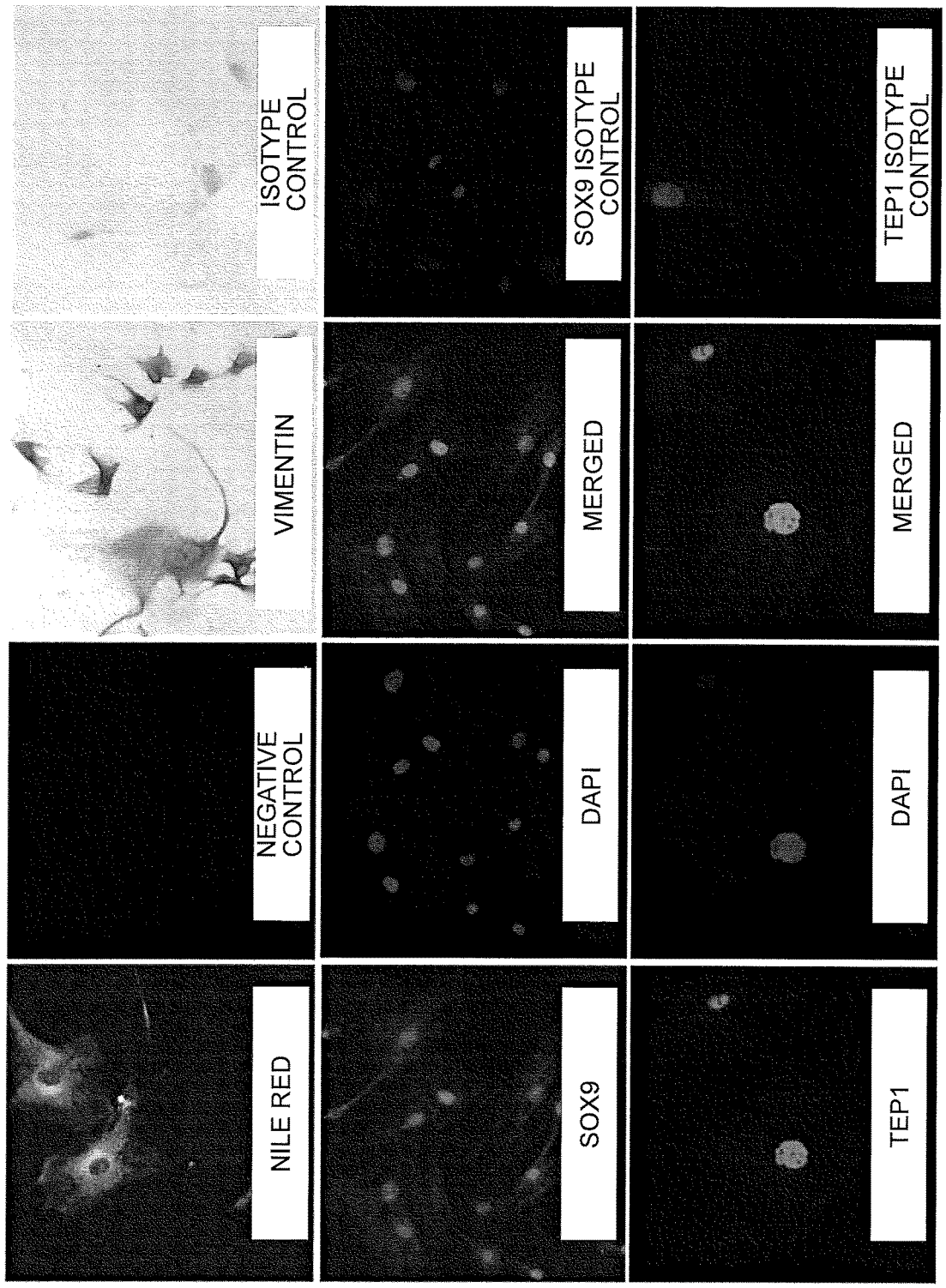
FIG. 2. Morphological characterization and Immortalization of human Sertoli cells. Upper panels left: Nile Red staining for characteristic lipid droplet accumulation. Upper panels right: Vimentin immunohistochemical staining. Middle panels: Immunofluorescence staining for SOX9. Bottom panels: Immunofluorescence staining for telomerase-associated protein 1 (TEP1) in immortalized Sertoli Cells.
Figure 3:
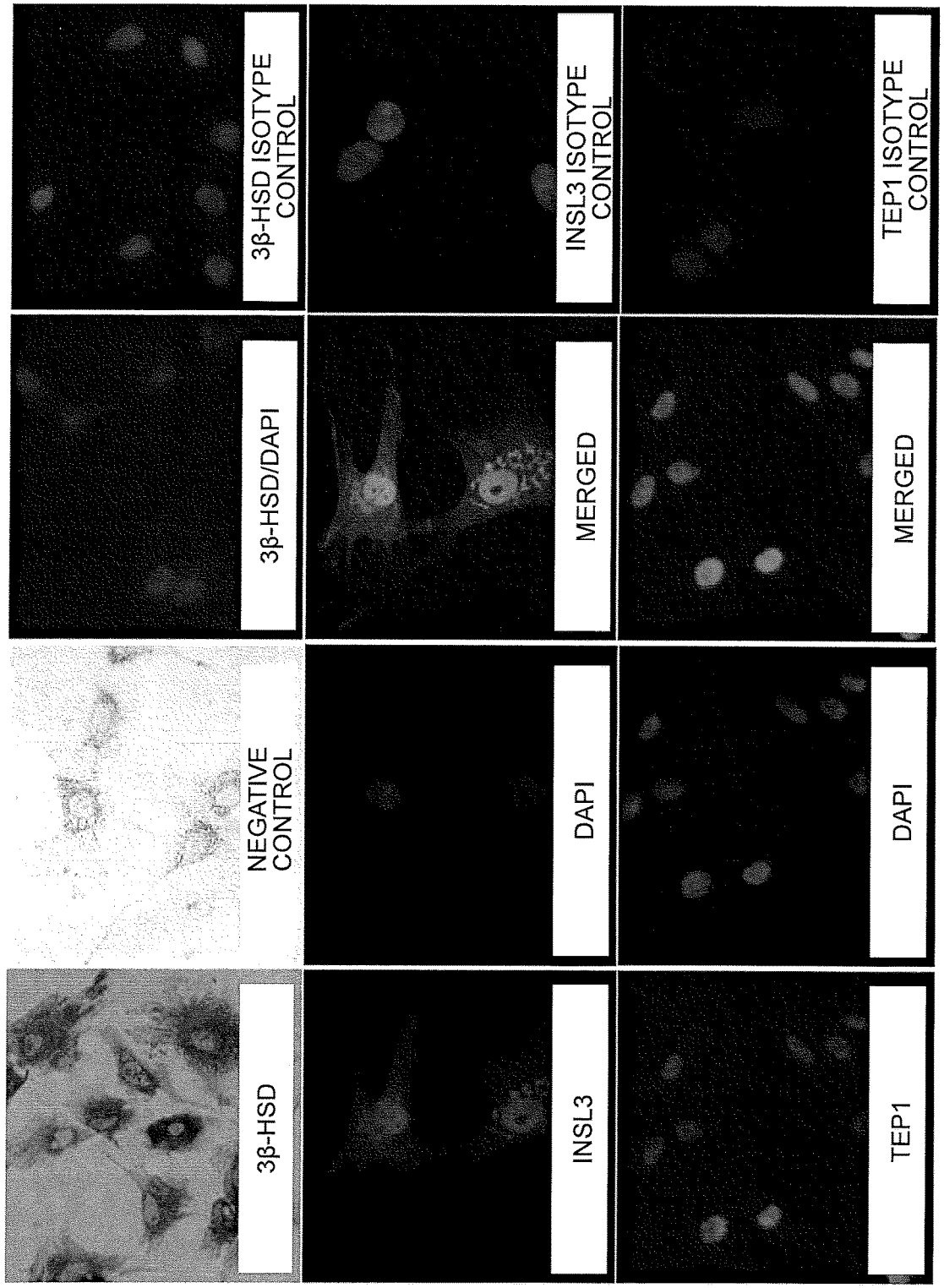
FIG. 3. Morphological characterization and Immortalization of human Leydig cells. Top panels: 3-β-hydroxysteroid dehydrogenase (3β-HSD) chemical staining. Middle panels: Immunofluorescence staining for INSL3. Bottom panels: Immunofluorescence staining for TEP1 in immortalized Leydig cells.
Figure 4A:
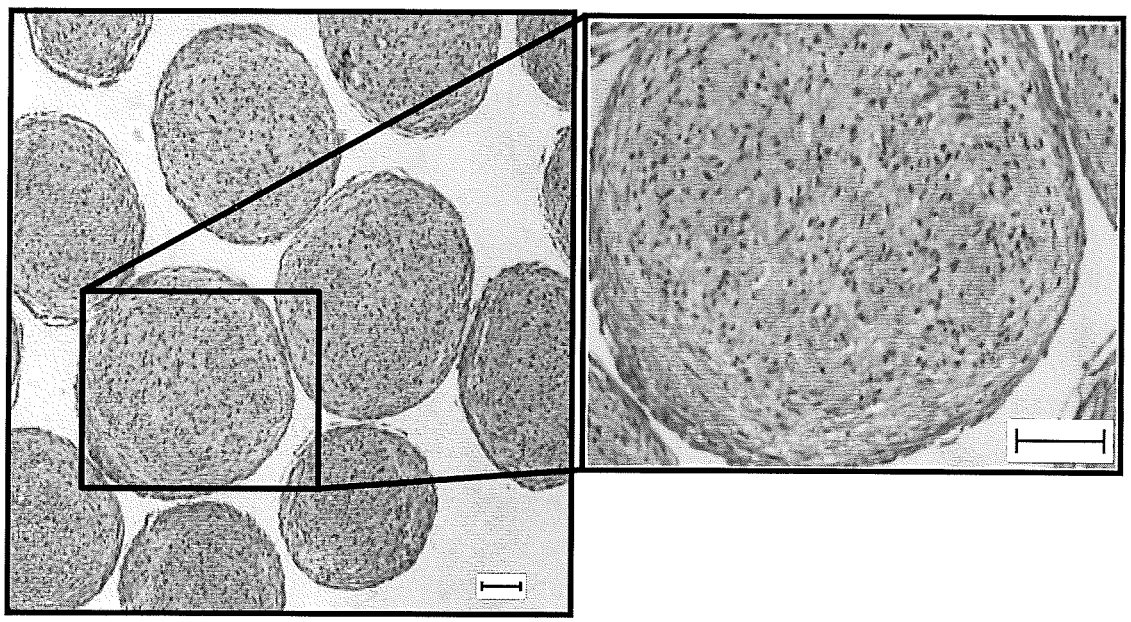
FIGS. 4A-4D. Initial testicular organoid morphology, viability, three-dimensional (3D) organization, and ultrastructural analysis.
Figure 4B:
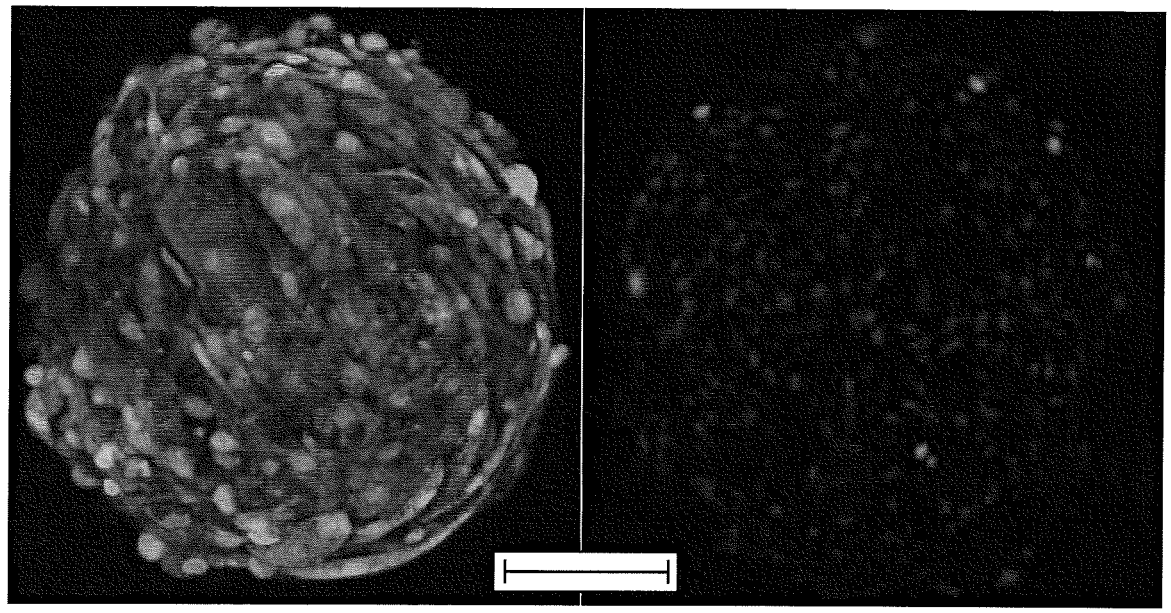

All 3D culture experiments were performed using established and characterized human SSC (FIG. 1A), Sertoli (FIG. 1B and FIG. 2), and Leydig (FIG. 1B and FIG. 3) primary cell cultures. These cells were first cultured in standard 2D tissue culture plates prior to being seeded into Perfecta3D® hanging drop plates in order to establish 3D cultures (Muschler, G., *Engineering principles of clinical cell-based tissue engineering.* J. Bone Joint Surg. Am. 86-A:1541-1558 (2004)). Multicellular testicular organoids formed within 24-48 hours and were then transferred to U-bottom 96-well ultra-low attachment plates for extended culture and analysis. As an initial baseline evaluation of internal morphology, organoids were harvested, paraffin embedded, and sectioned for H&E staining (FIG. 4A). In order to evaluate viability, organoids were stained using Live/Dead assays and subsequently evaluated for proliferation using immunostaining (FIG. 4B).

Spermatogonial stem cell, Sertoli, and Leydig cells have a tendency to proliferate significantly during culture on tissue culture plates or flasks. It was therefore important to assess the proliferative capacity of these cells in 3D culture. Accordingly, paraffin sections of early time point organoids were immunostained for Ki-67, a protein exclusively associated with cell proliferation (FIG. 4B).

Figure 4C:
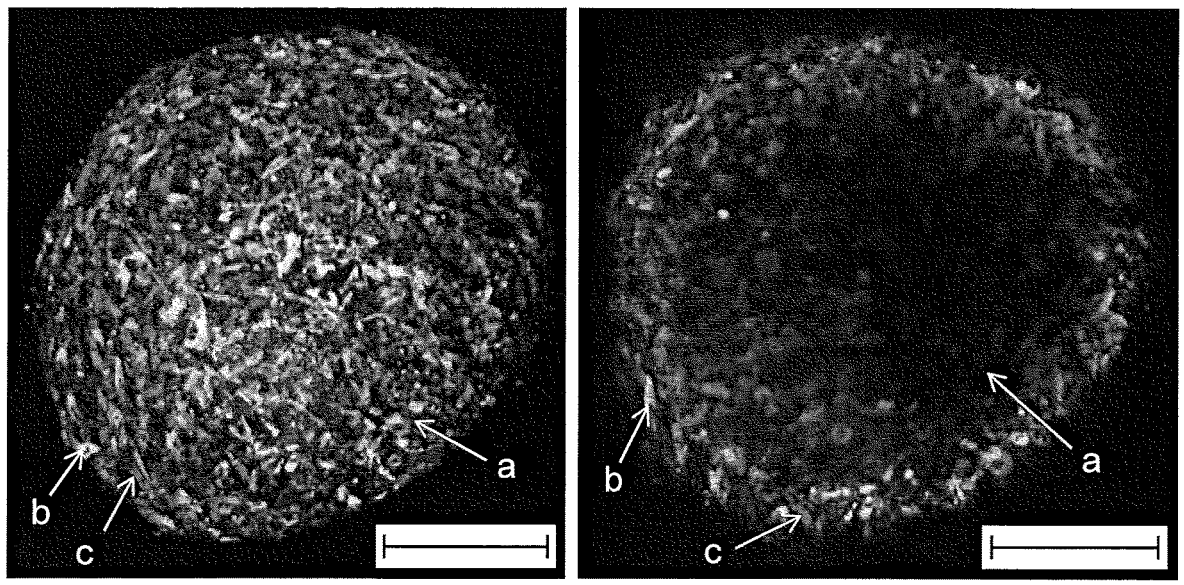

The presence of an intact SSC niche environment is critical for the correct differentiation of germ cells within the native tissue. This relationship between spermatogonial stem cells, Sertoli cells, and the interstitial signaling environment containing androgen-producing Leydig cells allows for not only structural support, but also provides the correct temporal and nutrient cues for successful differentiation. Thus, it was important to determine cell-specific organization within the organoids, since individual testicular cell types have significantly different growth properties and composition. An assay was designed to measure 3D organization after formation by using three fluorescent cell-surface markers. To accomplish this, each individual primary cell culture (SSC, Sertoli, Leydig) was stained with one of three available surface-labeling solutions. These fluorophores are not cytotoxic to cells and can remain detectable for several weeks in culture. Labeled cells were then combined into an organoid formation mixture at the determined cell ratio of 8:1:1 (SSC:Sertoli:Leydig) and cultured on 96-well hanging drop plates to form 3D cultures. After 48 hours, cultures were transferred to low-attachment 96-well round-bottom plates and evaluated for organizational changes over time (FIG. 4C). This analysis indicated that there was a propensity of the cells to self-organize during extended culture as indicated by the association of germ cells within the center of each organoid with somatic cells (particularly Leydig cells) targeting to the periphery of the structure.

Figure 4D:
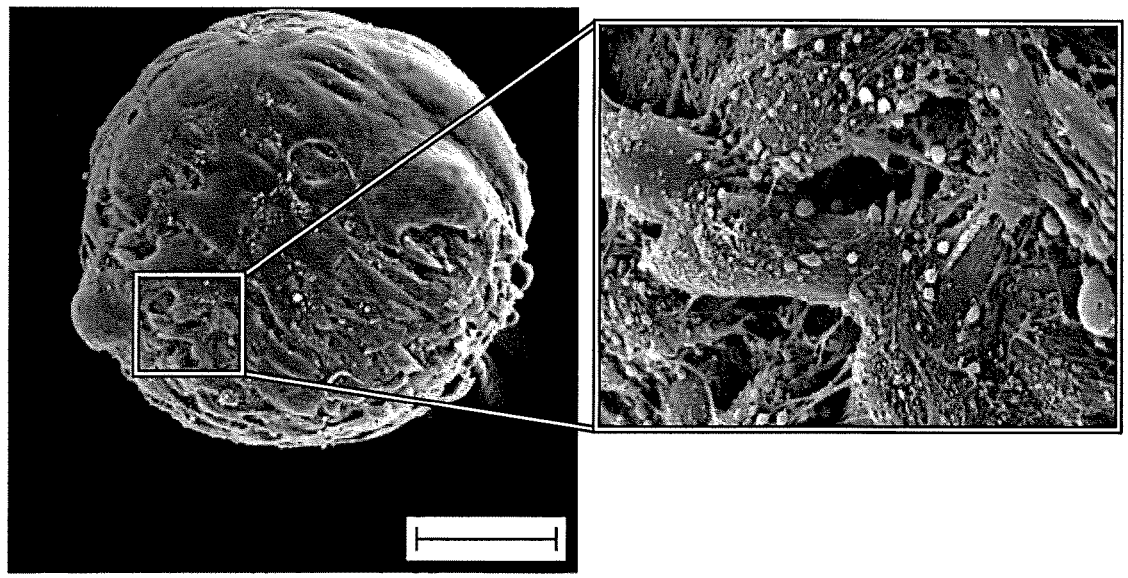

Ultrastructural characterization was an important consideration of this study to quantify differences in cell behavior in 3D culture as compared to corresponding cells using 2D culture methods. Scanning electron microscopy (SEM) was used to verify cellular associations observed during initial H&E staining. As seen in the H&E sections (FIG. 4A), significant extracellular matrix proteins appeared to be secreted by cells in the 3D structure. Sertoli cells produce large amounts of ECM proteins including laminin, collagens I and IV, and fibronectin in the native tissue. Dense and complex cellular organization around the exterior of the organoid, with visible extensions and filopodia were observed in representative scanning electron micrographs and provided a high-resolution view of the external architecture of these cultures (FIG. 4D).

Example 9

Figure 5C:
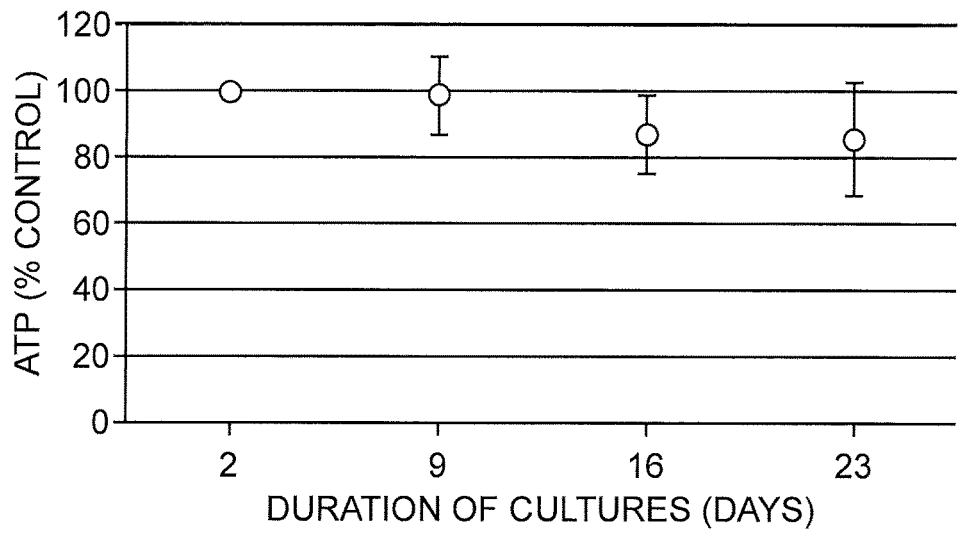

Long-term Morphological Characteristics and Viability of Multicellular Human Testicular Organoids In Vitro Basic long-term viability was established in testicular organoid cultures. Specifically, organoids were harvested after 2, 9, 16, and 23 days of culture and examined for morphological characteristics, viability, and internal organization. At day 2 organoids appeared uniform and tightly packed with cells (FIG. 5A, Panel I). By day 9 the density of cell nuclei decreased, as significantly more extracellular matrix (ECM) was produced within the structure (FIG. 5A, Panel II). By day 23, organoids were found to have increased in size from approximately 250 μm to ~400 μm, most probably due to ECM production, with no obvious signs of necrosis (FIG. 5A, Panel IV). Viability at each time point was assessed using confocal microscopy after Live/Dead staining and ATP quantitation. No significant cell death was observed during the 23 day culture period for any organoid (FIG. 5B, Panels I-IV). ATP assays (CellTiter-Glo® Promega) showed that the organoids (n=6) maintained greater than 85% viability throughout the entire culture period (FIG. 5C).

Example 10

Figure 6A:
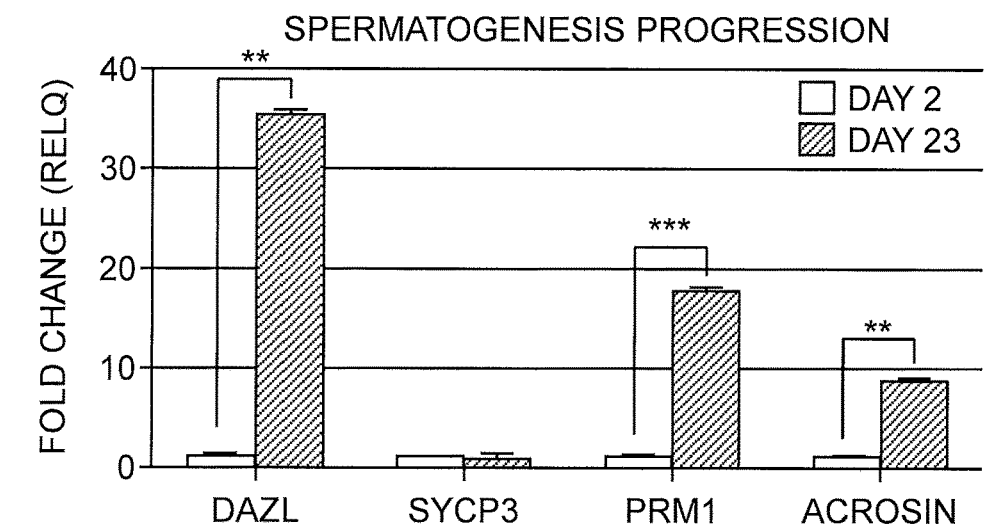
FIGS. 6A-6F. Testicular organoid gene expression changes following 23 days in culture. The fold change (RelQ, 2-ΔΔCT) for stage-specific spermatogenesis markers and somatic cell functional markers (FIG. 6A) revealed a significant upregulation of spermatogenesis (DAZL, ACR, PRM1) genes and a significant upregulation of both Leydig (3β-HSD, CYP11a1) and Sertoli (FSHr, CYP19a1) functional markers. A significant change in gene expression for undifferentiated spermatogonia (UCHL1, PLZF) was not observed, however these genes maintained consistent expression for the entire culture period (n=40). Data presented as mean±SD. Significance: *p<0.05; p<0.01; *p<0.001; ****p<0.000. Evaluation of post-meiotic germ cell markers in differentiated human testicular organoids for PRM1 (FIG. 6B) and Acrosin (FIG. 6C). Immunofluorescence staining of post meiotic markers, PRM1 (FIG. 6D) and Acrosin (FIG. 6E), on human adult testis sections were used as positive controls. Scale bar 5 μm. Quantification of secreted testosterone over time by testicular organoids (FIG. 6F) measured with ELISA (n=10). Data presented as mean±SD. Significance: *p<0.05.
Figure 6A:
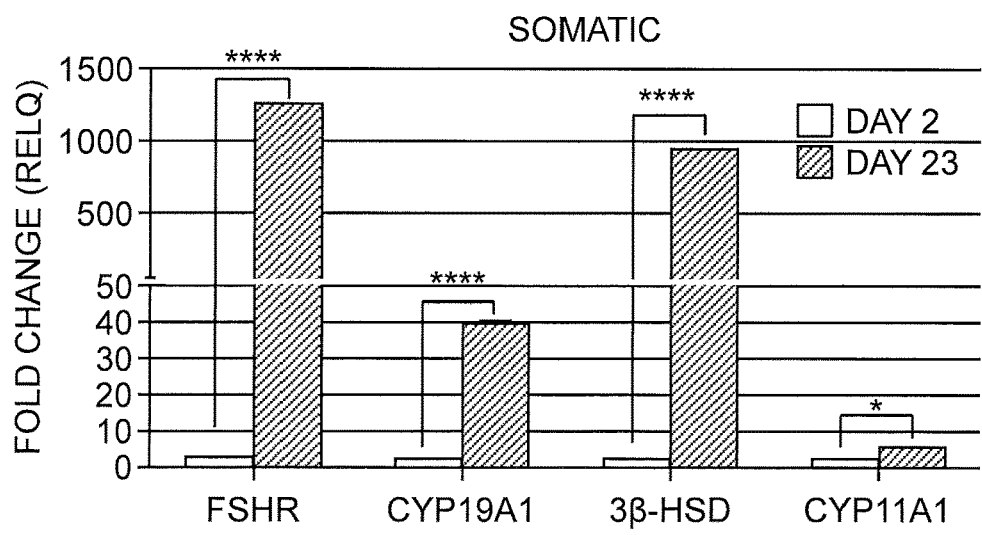

Transcriptional Changes of Functional and Stage-Specific Genes During Extended Culture Gene expression of somatic cell functional markers and spermatogenesis-specific genes was evaluated in human testicular organoid cultures over time (FIG. 6A). Of these markers, there was no significant increase in the expression level of SYCP3, a meiotic germ cell marker, detected during the culture period. However, the spermatogonial marker DAZL, which is expressed in differentiating spermatogonia (nuclear) through meiosis (cytoplasmic) and in round spermatids, was significantly upregulated over time with a fold-change of 35.28 at day 23. Significant increases in the post-meiotic germ cell markers PRM1 (18-fold increase) and Acrosin (9-fold increase) occurred (FIG. 6A), indicating in vitro germ cell differentiation. In vitro somatic cell function was assessed via gene expression changes for Sertoli and Leydig cell functional markers FSHr, CYP19A1, CYP11A1, and 3β-HSD, which showed fold changes of 1268.74, 39.47, 4.75 and 940.92, respectively (FIG. 6A). All quantitative RT-PCR data were normalized to the house keeping gene POLR2A as an internal control.

Example 11

Expression of Post-Meiotic Germ Cell Markers During Extended Culture

Figure 6B:
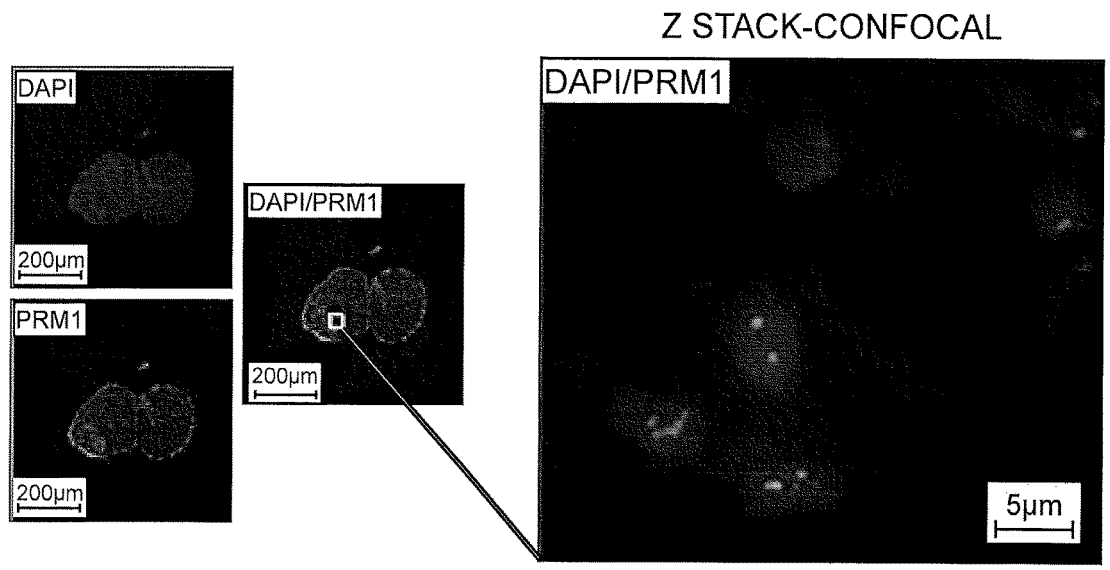
Figure 6C:
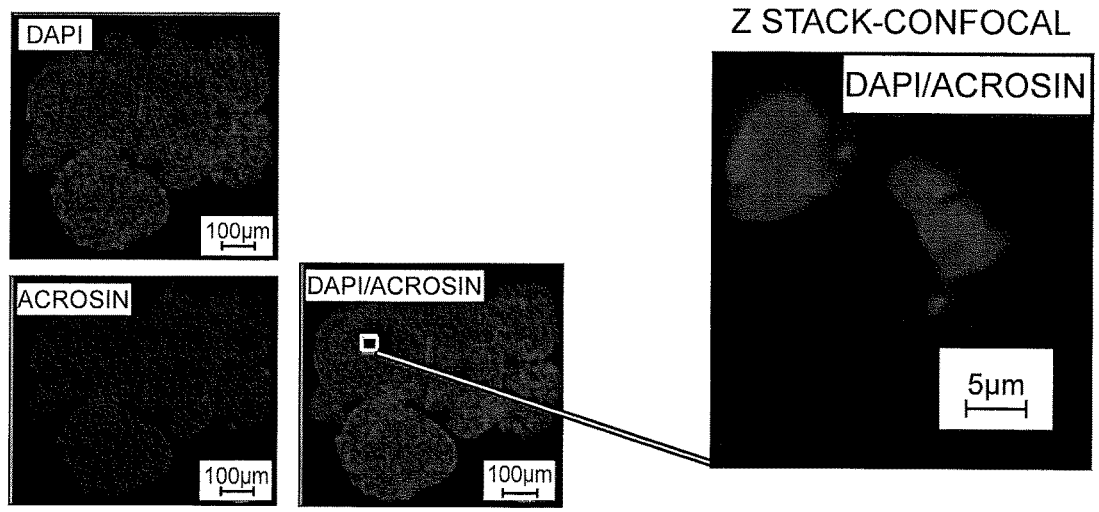
Figure 6D:
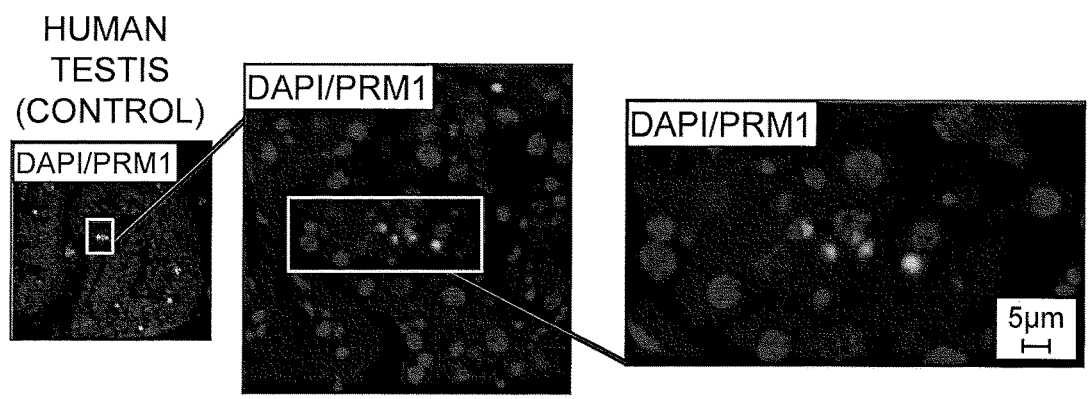
Figure 6E:
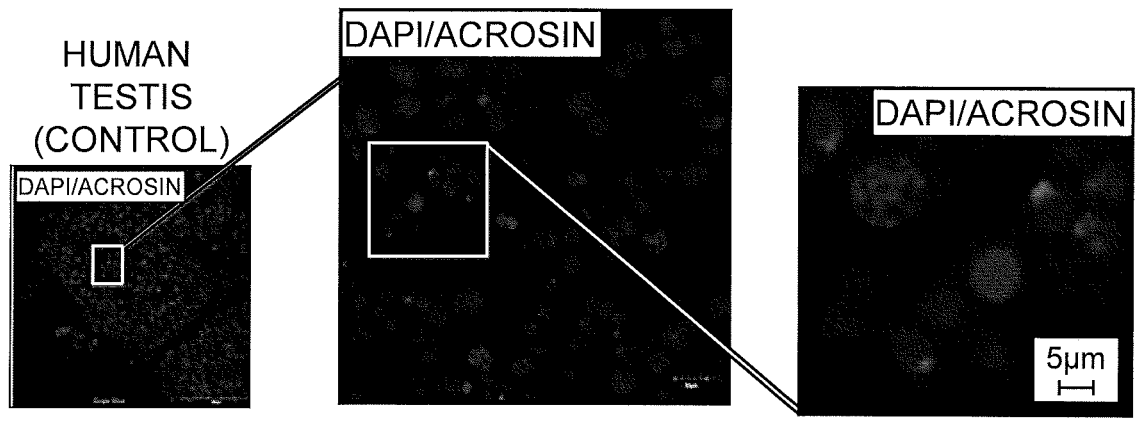

Detection of post-meiotic germ cell markers at the transcript level was confirmed via immunostaining of differentiated testicular organoids following culture for 23 days. Positive cells for PRM1 (FIG. 6B) and Acrosin (FIG. 6C) could be localized in differentiated organoids. Human adult testis tissue was stained as positive control (FIG. 6D and FIG. 6E).

Example 12

Figure 6F:
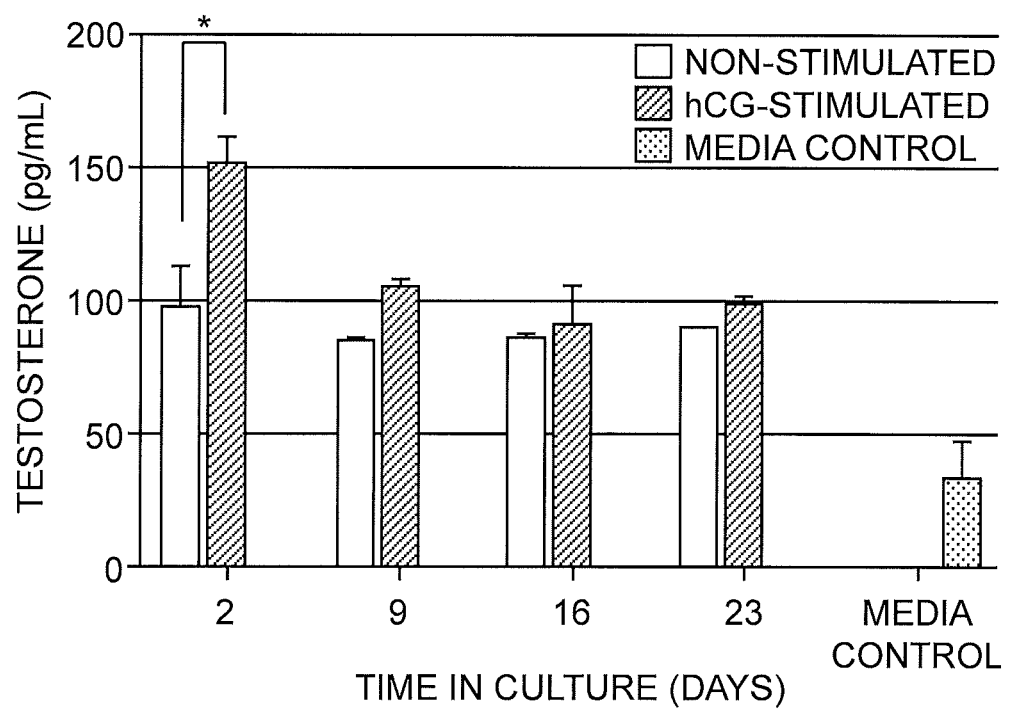

Multicellular Human Testicular Organoids can be Stimulated to Produce Androgens During Extended Culture To test the ability of 3D human testicular organoids to produce androgens and respond to androgen stimulation in vitro, culture supernatant was measured for total testosterone (n=10) concentration per 100,000 cells before and after stimulation with 2 ng/mL hCG for 3 hours. At day 2, nonstimulated testosterone concentrations were 97.168±17.471 pg/mL, whereas after hCG stimulation, concentrations were 151.325±11.592 pg/mL (FIG. 6F). Stimulation at day 2 resulted in testosterone levels significantly higher than nonstimulated cells (p=0.00039). Subsequent measurements for days 9, 16, and 23 revealed consistent testosterone production of 85.03±2.447, 85.56±2.31, and 89.376±0.891 pg/mL/100,000 cells respectively. Organoids appeared to lose responsiveness to repeated hCG stimulation as, over time, Testosterone concentrations slightly decreased from 105.958±2.556 at day 9 to 91.008±14.764 and 98.83±3.495 at days 16 and 23, respectively (FIG. 6F).

Example 13

Evaluation of Human Testicular Organoids as a Reproductive Toxicity Model

Figure 7C:
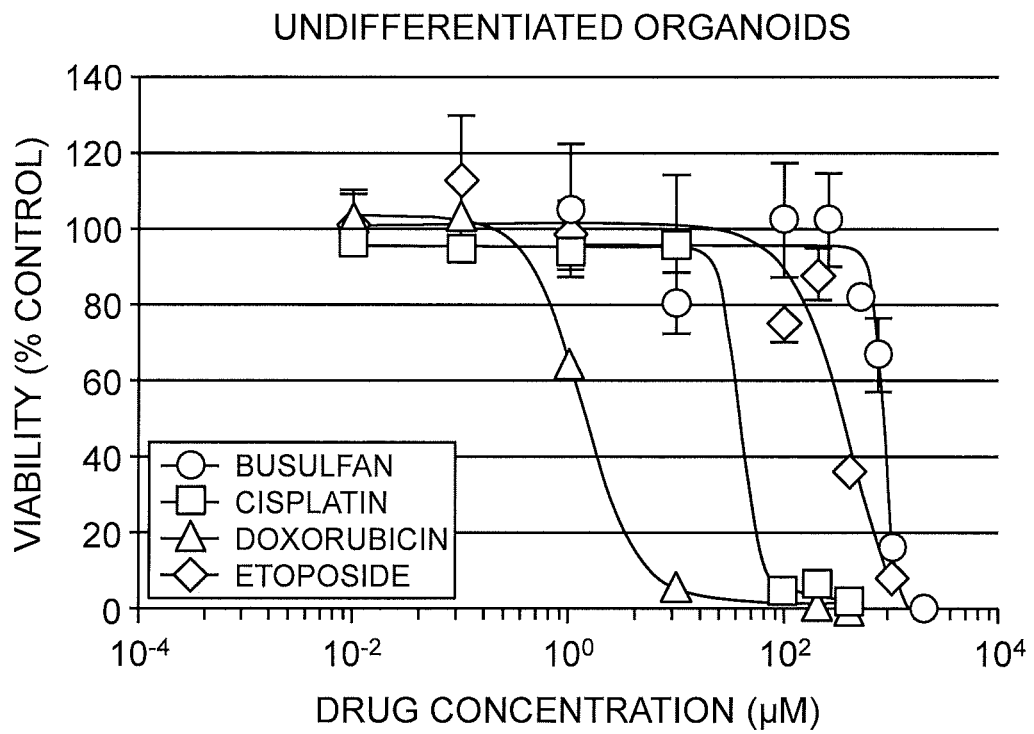
Figure 7C:
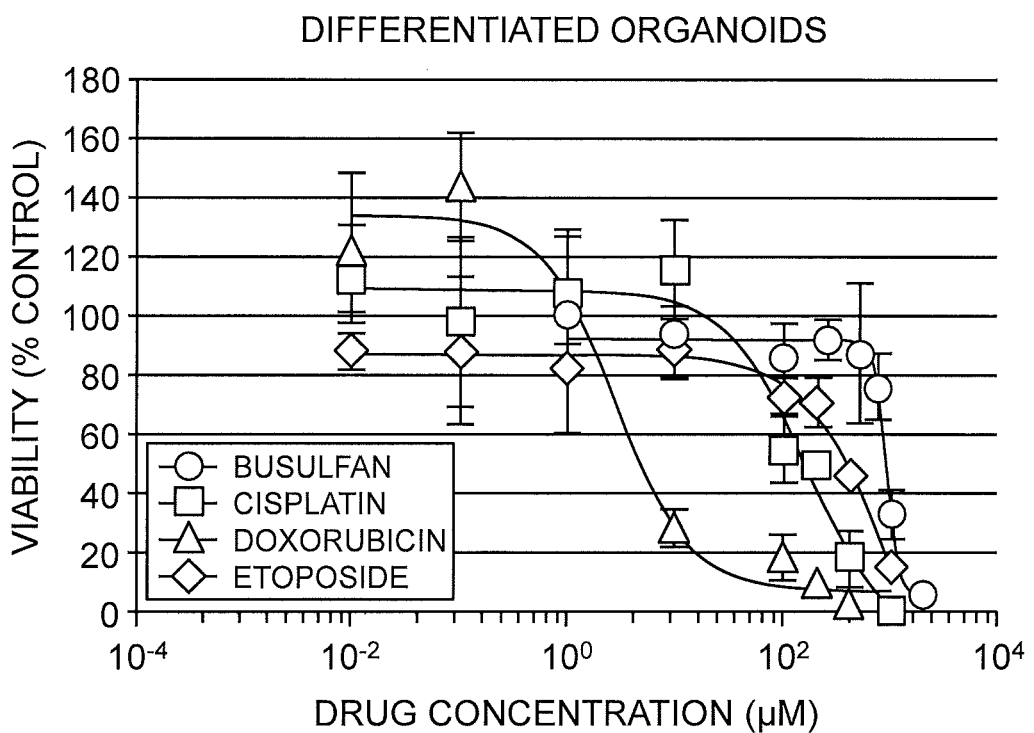
Figure 7D:
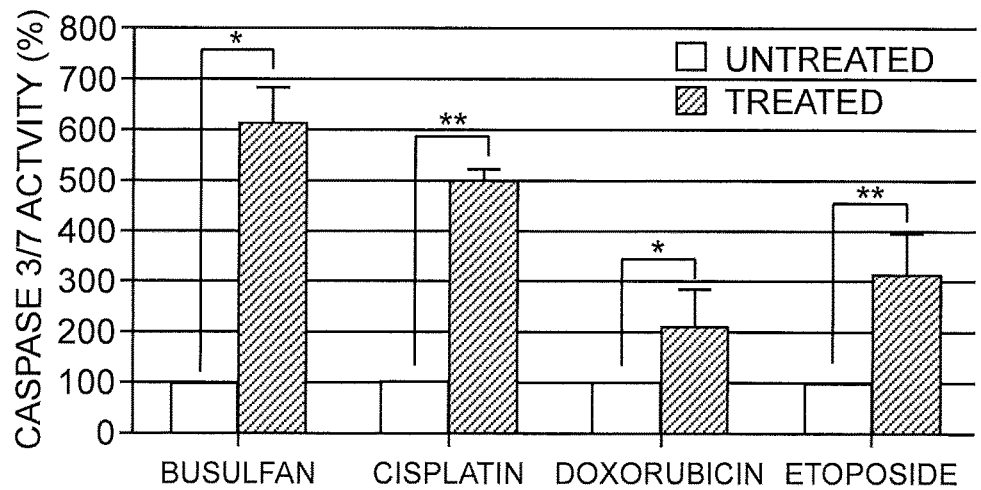
Figure 7E:
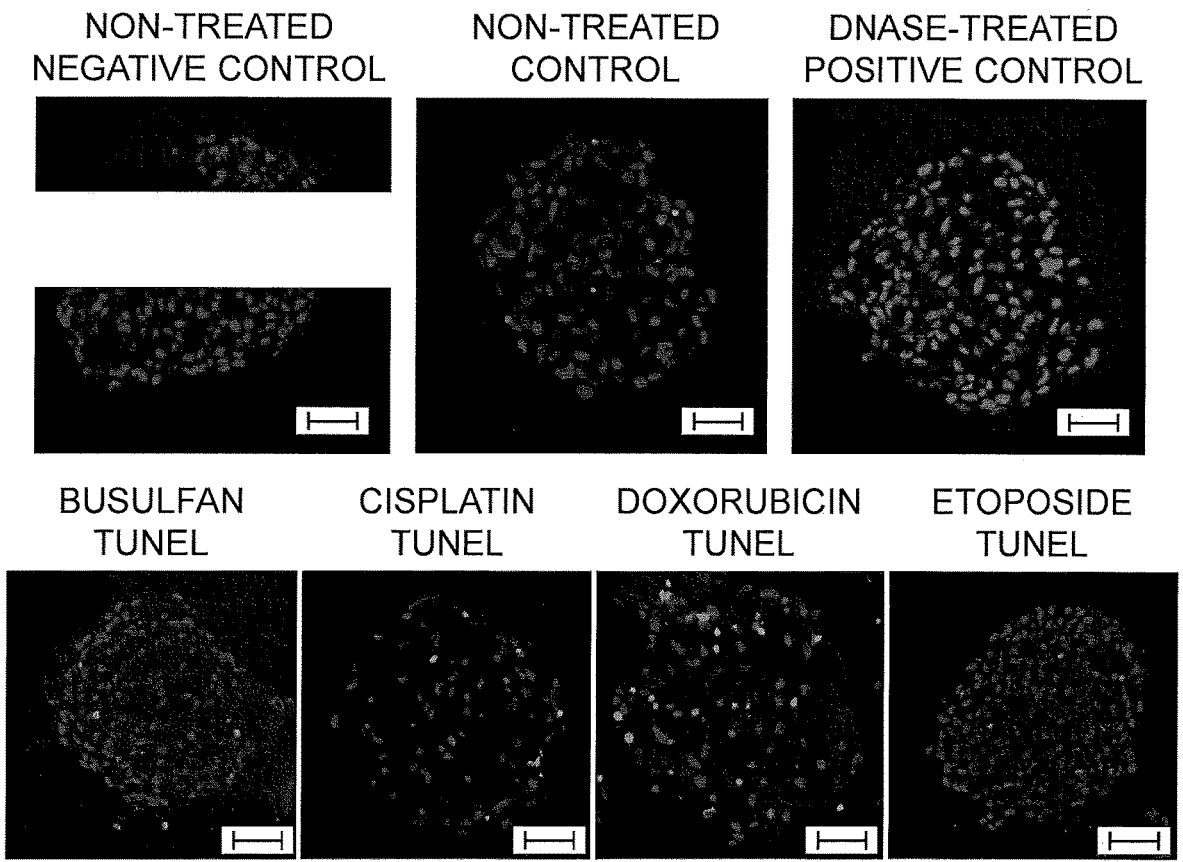

The use of human testicular organoids as a novel screening tool for reproductive toxicity was assess by exposing 3D organoids to four clinically relevant antimitotic chemotherapeutic drugs: busulfan, cisplatin, doxorubicin, and etoposide. To obtain $IC_{50}$ values, undifferentiated (2 days in culture) and differentiated (23 days in culture) organoids were exposed to increasing concentrations of drugs for 48 hours. H&E staining as well as Live/Dead viability assays were performed on organoids following drug treatment (FIG. 7A and Figure B, respectively). Drug-treated organoids were harvested and further evaluated for toxicity by measuring ATP production (CellTiter-Glo®; Promega, Madison, Wis.). Resulting viability was then used to establish $IC_{50}$ values for organoid cultures (FIG. 7C). 3D organoids under all drug treatment conditions, either undifferentiated or differentiated organoids, exhibited a dose-dependent decrease in viability and maintained $IC_{50}$ values significantly higher than corresponding 2D cultures (Table 1). Caspase 3/7 activity (FIG. 7D) and TUNEL assay (FIG. 7E) following 48-hour exposure to the four drugs showed significant increases in organoid cell apoptosis.

TABLE 1

| Drug | 2D $IC_{50}$ (μM) | 3D $IC_{50}$ (μM) | |
| --- | --- | --- | --- |
| | | Undifferentiated Organoids | Differentiated Organoids |
| Busulfan | 327.8 | 829.7 | 905.9 |
| Cisplatin | 23.80 | 38.42 | 157.7 |
| Doxorubicin | 0.1902 | 1.330 | 2.757 |
| Etoposide | 43.49 | 449.3 | 838.8 |

Example 14

Cryopreservation and Viability Assessment of Human Testicular Organoids

Figure 8A:
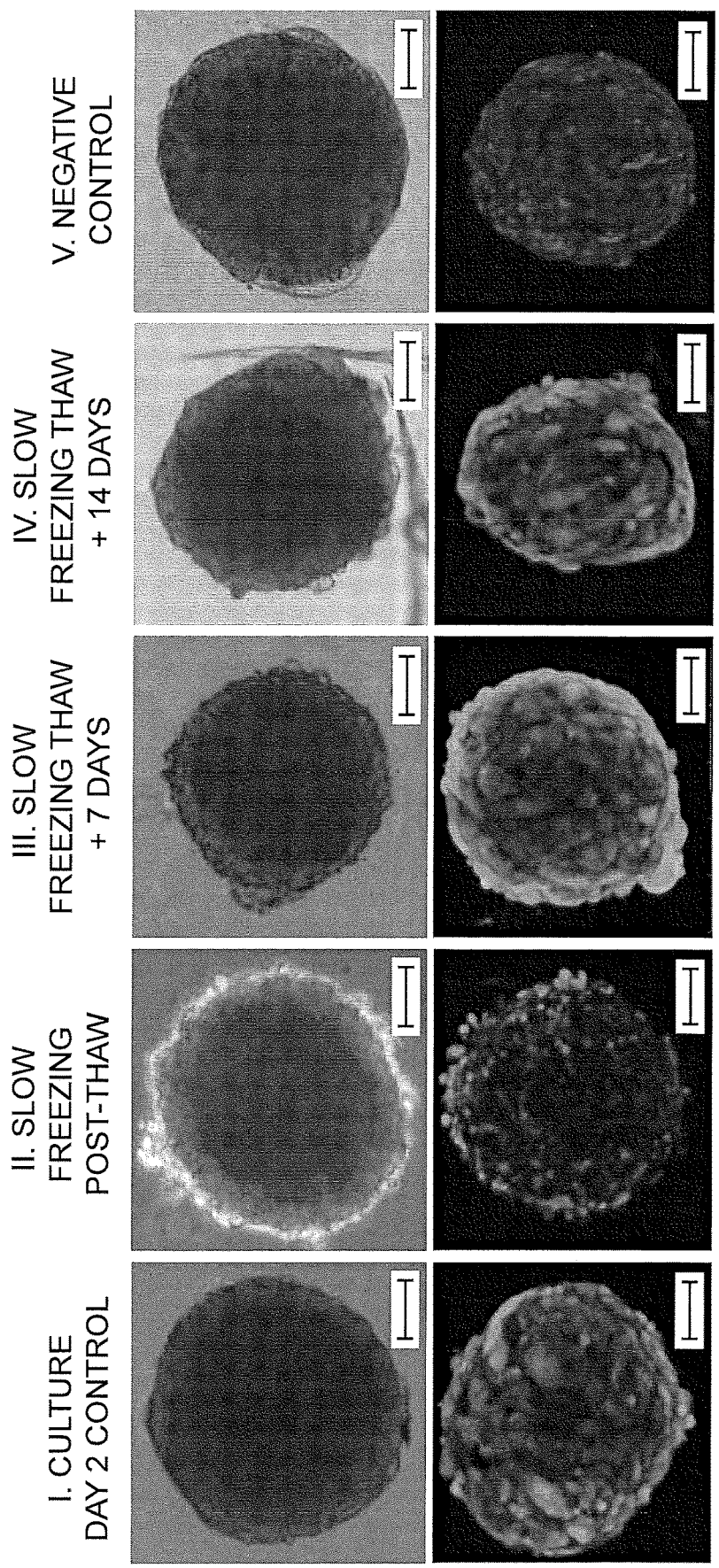
FIGS. 8A-8B. Morphological and viability assessment of cryopreserved human testicular organoids.
Figure 8B:
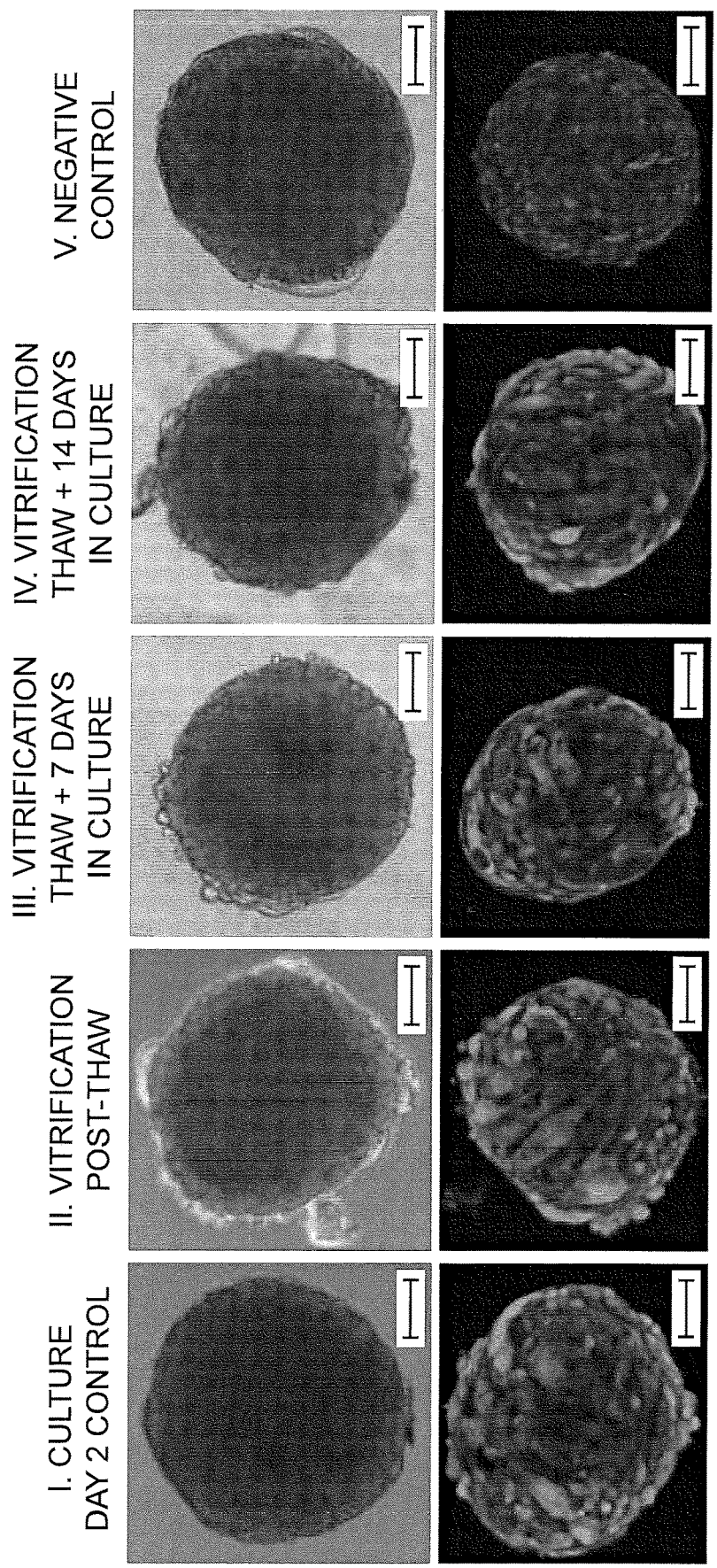

The feasibility of cryopreserving organoids for long-term storage and distribution was evaluated using two distinct cryopreservation protocols. First, organoids were cryopreserved using a standard SSC freezing protocol including MEM supplemented with 20% FBS and 8% DMSO (slow freezing). After 7 days of liquid nitrogen storage, organoids were thawed and their morphology and viability were determined via phase contrast microscopy and fluorescent Live/Dead staining followed by macro confocal microscopy. These assays were performed immediately after thawing and again at 7 and 14 days post-thawing. When compared to control samples obtained at day 2 of normal culture (FIG. 8A), the cryopreserved and thawed organoids appeared to be stressed, as indicated by the small compact cellular phenotype of the cells within the organoid. However, no significant cell death was observed within the structure. By day 7 post-thaw, the cells within the organoid had visibly recovered and displayed a normal phenotype. No significant cell death was observed within organoids cryopreserved in this manner and organoids maintained greater than 90% viability for the duration of the 14 day culture period (FIG. 8A). Vitrification was also evaluated as a method of cryopreservation, following a protocol routinely used to preserve human embryos for in vitro fertilization (IVF). Organoids were vitrified, kept frozen for 7 days, and thawed using standard thawing methods for vitrified human embryos (Kuwayama, M., et al., *Comparison of open and closed methods for vitrification of human embryos and the elimination of potential contamination.* Reprod. Biomed. Online, 11:608-614 (2005); Yokota, Y., et al., *Birth of a healthy baby following vitrification of human blastocysts.* Fertil. Steril. 75:1027-1029 (2001)). The organoids were then cultured at 34° C. and 5% $CO_2$ for 14 days. Compared to organoids cryopreserved slowly in DMSO, vitrified organoids appeared less stressed and analysis revealed that vitrified organoids maintained greater than 95% viability after thawing and for the subsequent 14 days of additional culture (FIG. 8B).

The results of this analysis demonstrated the enhanced feasibility of using this system for high-throughput in vitro drug screening applications. By establishing that these organoids can be successfully cryopreserved for future use without sacrificing proliferative capacity or functionality, this system is applicable to high-throughput applications.

Example 15

Human Testicular Organoids from Immature Testicular Cells

The feasibility of establishing a 3D organoid system using immature testicular cells was assessed. Testicular organoids have the potential application of fertility preservation in prepubertal male cancer survivors and genetically impaired boys who are at risk of infertility.

Material and Methods.

Human testes recovered from a 10-year-old brain dead subject was obtained via the NDRI. Immaturity of the testicular tissue was confirmed by performing histological evaluation in addition to Q-PCR and immunohistochemistry for undifferentiated and differentiated germ cell markers. To establish 2D testicular cell culture to propagate four major testicular cell types including spermatgonia, Sertoli, Leydig and peritubular cells, two-step enzymatic digestion was performed on tissue and cells were seeded on plastic in enriched StemPro® medium. Isolated cells were cultured for more than 50 days and 5 passages. Specific gene expression assays were used to demonstrate the presence of all 4 cell types and confirm the undifferentiated condition of spermatogonial cells. (Peritubular cells were included in an amount of about 1% of the total cells.) To evaluate the quantity of each cell type, flow cytometry analysis was used. Subsequently, the 2D cultured cells were integrated into 3D spherical culture via hanging drop method, using 10,000 cells per organoid. The structure of 3D human testicular organoids was examined by H&E staining. Viability and metabolic activity of organoids was evaluated each week using Live/Dead cell staining and an ATP production assay.

Results.

Figure 9A:
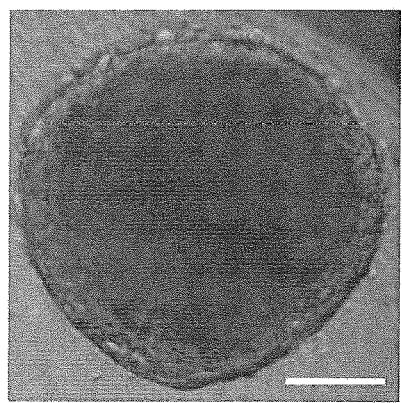
FIGS. 9A-9C. Human 3D Testicular from immature testicular cells, after 3 weeks in culture.
Figure 9B:
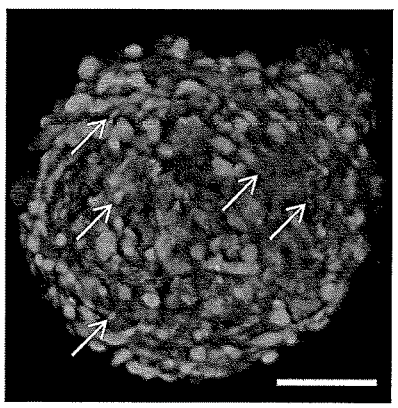
Figure 9C:
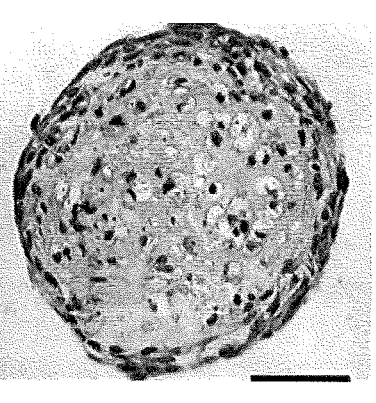

Morphological evaluation of the tissue and immunohistochemical staining for PRM1 and Acrosin (as germ cell differentiation markers) established the immaturity of the tissue and the isolated cells. Gene expression analysis and the presence of markers for spermatogonia (i.e., PLZF, UCHL1, THY1, CD9, FGFR3 and SSEA4); Sertoli cells (i.e., GATA4, SOX9, Clusterin, and CD49f) Leydig cells (i.e., STAR, TSPO and Cyp11A1); and peritubular cells (i.e., CD34) indicated that each of the different cell types were isolated, cultured and integrated into 3D organoid. The 3D testis organoids system maintained their structure, viability and metabolic activity over 3 weeks of culture (FIGS. 9A-9C). This analysis demonstrated that human 3D testicular organoids were successfully generated using isolated human SSC, Sertoli, Leydig and peritubular cells from immature testis could be maintained in long term culture.

The foregoing is illustrative of the present invention, and is not to be taken as limiting thereof. The invention is defined by the following claims, with equivalents of the claims to be included therein.

That which is claimed is:

1. A cell composition in the form of a three-dimensional artificial testicular construct, the composition comprising, in combination:
 (a) spermatogonial stem cells, wherein said spermatogonial stem cells are not immortalized,
 (b) immortalized Sertoli cells, and
 (c) immortalized Leydig cells, wherein said three-dimensional construct is in the form of an organoid and has a diameter of 100 to 300 microns, and wherein said spermatogonial stem cells, immortalized Sertoli cells and immortalized Leydig cells are human cells.

2. The cell composition of claim 1, wherein:
(i) said spermatogonial stem cells are included in an amount by number of cells of from 70 to 90 percent;
(ii) said immortalized Sertoli cells are included in an amount by number of cells of from 5 to 20 percent; and
(iii) said immortalized Leydig cells are included in an amount by number of cells from 5 to 20 percent.

3. The cell composition of claim 1, wherein the ratio of (a):(b):(c) is 8:1:1.

4. The cell composition of claim 1, further comprising peritubular cells.

5. A culture composition comprising the cell composition of claim 1 in an aqueous culture medium, said culture media further comprising at least one extracellular matrix (ECM) protein.

6. The culture composition of claim 5, wherein said ECM protein comprises laminin, collagen type I, collagen type IV, fibronectin, elastin, or a combination thereof.

7. The culture composition of claim 5, wherein said ECM protein comprises collagen type I.

8. The culture composition of claim 5, wherein said at least one ECM protein is included in an amount of from 10 nanograms per milliliter to 1 milligram per milliliter.

9. The cell composition of claim 1, wherein said construct is provided in a biocompatible device.

10. The cell composition of claim 9, wherein the construct is produced via a scaffold-free platform.

11. The cell composition of claim 9, wherein the total number of all cells in said construct is from 100 to 10,000.

12. The cell composition of claim 9, characterized by:
(i) the production or expression of testosterone by said construct;
(ii) the expression of spermatogonial cell markers UCHL1, ITGA6, cKIT, DAZL, or a combination thereof;
(iii) the expression of Leydig and Sertoli cell markers HSD3B1, CYP11a1, FSHr, CYP19a1, cKIT, or a combination thereof;
(iv) the expression of meiotic and post-meiotic markers SYCP3, PRM1, ACROSIN, or a combination thereof; or
(v) a combination of (i)-(iv).

13. The cell composition of claim 9, wherein said construct has an outer cell layer comprising filopodia.

14. The cell composition of claim 9, wherein a central region of the construct comprises said spermatogonial stem cells.

15. A composition comprising:
(a) a hydrogel; and
(b) a plurality of cell compositions in the form of artificial three-dimensional testicular constructs according to claim 1,
wherein said plurality is provided in a biocompatible device,
wherein said cell compositions are provided in said hydrogel, and
wherein said hydrogel is a crosslinked hydrogel.

16. A biocompatible device, comprising
(a) a substrate having at least one chamber formed therein; and
(b) at least one artificial three-dimensional testicular construct provided in said chamber, said construct comprising a cell composition according to claim 1,
where said chamber has an inlet opening and outlet opening formed therein.

17. A method of screening a compound for pharmacological or toxicological activity, comprising:
(a) providing the device of claim 16,
(b) administering a compound to said construct; and
(c) detecting a pharmacological or toxicological response from at least one cell of said device.

18. The method of claim 17, wherein said response comprises cell death; cell growth; absorption, distribution, metabolism, or excretion (ADME) of said compound; or upregulation or downregulation of production of a compound by said at least one cell.

19. The method of claim 18, wherein said cell death comprises senescence or apoptosis.

20. The method of claim 18, wherein said cell growth comprises benign or metastatic cell growth.

21. A biocompatible device, comprising
(a) a substrate having at least one chamber formed therein; and
(b) at least one artificial three-dimensional testicular construct provided in said chamber, each construct comprising a cell composition according to claim 1,
wherein said device is packaged in a container with a transient protective support medium in said chamber in gelled form.

22. A method of making a device, comprising:
(a) providing a substrate and;
(b) depositing at least one cell composition of claim 1 on said substrate.

23. The method of claim 22, wherein said depositing step is carried out by bioprinting, pipetting, microinjection, or microfluidic deposition.

* * * * *

UNITED STATES PATENT AND TRADEMARK OFFICE
CERTIFICATE OF CORRECTION

PATENT NO. : 10,993,433 B2  
APPLICATION NO. : 15/294154  
DATED : May 4, 2021  
INVENTOR(S) : Pendergraft et al.

Page 1 of 1

It is certified that error appears in the above-identified patent and that said Letters Patent is hereby corrected as shown below:

In the Specification

Column 8, Line 43: Please correct "(aMEM)" to read -- (αMEM) --

Column 22, Line 47: Please correct "MCT" to read -- ΔΔCT --

Column 25, Line 44: Please correct "-400 μm" to read -- ~400 μm --

Signed and Sealed this  
Seventh Day of September, 2021

Drew Hirshfeld  
*Performing the Functions and Duties of the*  
*Under Secretary of Commerce for Intellectual Property and*  
*Director of the United States Patent and Trademark Office*